(12) United States Patent
Mooney

(10) Patent No.: US 10,307,640 B2
(45) Date of Patent: Jun. 4, 2019

(54) APPARATUS AND METHOD FOR ANALYZING A GOLF SWING

(76) Inventor: Brian Francis Mooney, Dublin (IE)

(*) Notice: Subject to any disclaimer, the term of this patent is extended or adjusted under 35 U.S.C. 154(b) by 1405 days.

(21) Appl. No.: 14/345,626

(22) PCT Filed: Sep. 13, 2012

(86) PCT No.: PCT/EP2012/068008
§ 371 (c)(1),
(2), (4) Date: May 30, 2014

(87) PCT Pub. No.: WO2013/041444
PCT Pub. Date: Mar. 28, 2013

(65) Prior Publication Data
US 2014/0342844 A1    Nov. 20, 2014

(30) Foreign Application Priority Data
Sep. 20, 2011 (IE) .................................. S2011/0430

(51) Int. Cl.
| | | |
|---|---|---|
| A63F 9/24 | (2006.01) |
| A63F 13/00 | (2014.01) |
| G06F 17/00 | (2019.01) |
| G06F 19/00 | (2018.01) |
| A63B 24/00 | (2006.01) |
| G06K 9/00 | (2006.01) |
| A63B 69/36 | (2006.01) |

(52) U.S. Cl.
CPC .......... *A63B 24/0006* (2013.01); *A63B 69/36* (2013.01); *G06K 9/00342* (2013.01)

(58) Field of Classification Search
CPC ............ A63B 24/0003; A63B 24/0006; A63B 24/0015; A63B 24/0025
See application file for complete search history.

(56) References Cited

U.S. PATENT DOCUMENTS 5,625,577 A    4/1997  Kunii et al.
5,772,522 A *  6/1998  Nesbit ............... A63B 24/0003
                                                 434/252
(Continued)

FOREIGN PATENT DOCUMENTS

JP    2013-027628    2/2013
JP    2013-090862    5/2013
(Continued)

OTHER PUBLICATIONS

Notice of Reason(s) for Rejection, dated Dec. 5, 2016 for corresponding Japanese Patent Application No. 2014-531177 with English language translation (12 pages).
(Continued)

*Primary Examiner* — Milap Shah
*Assistant Examiner* — Jason Pinheiro

(57) ABSTRACT

The system analyzes a golf swing, determining individual joint powers generated in a player's body with high levels of accuracy, using inverse dynamics and detailed modelling of the player's body. A depth camera is used to measure body segment shapes and a magnetic motion capture system and 3D force plate system used to measure swing parameters. The system produces an expeditious analysis without the need for highly skilled technical personnel and is suitable for individual coaching and compilation of large golf swing databases.

48 Claims, 13 Drawing Sheets

(56) References Cited

U.S. PATENT DOCUMENTS

Figure 2:
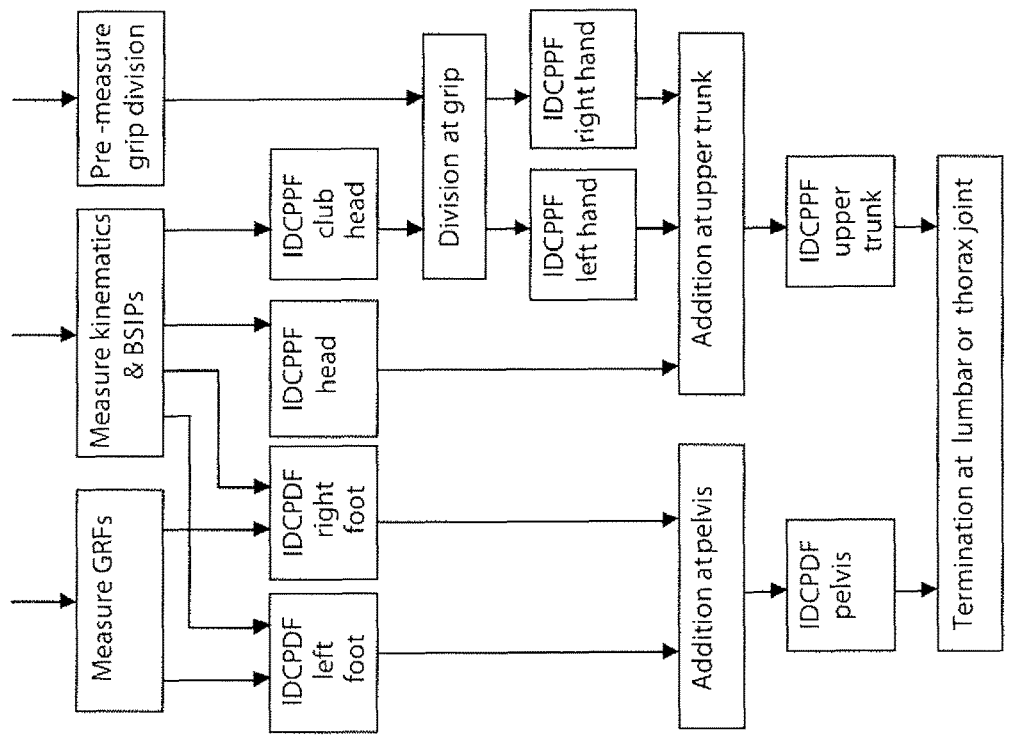

| | | | | |
|---|---|---|---|---|
| 6,050,963 | A * | 4/2000 | Johnson | A61B 5/1124 600/587 |
| 6,697,820 | B1 | 2/2004 | Tarlie | |
| 6,778,866 | B1 | 8/2004 | Bettwy | |
| 7,403,202 | B1 | 7/2008 | Nash | |
| 8,678,943 | B2 * | 3/2014 | Mooney | A63B 69/36 473/219 |
| 8,696,450 | B2 * | 4/2014 | Rose | G09B 19/0038 463/30 |
| 2002/0064764 | A1 | 5/2002 | Fishman et al. | |
| 2008/0170123 | A1 | 7/2008 | Albertson et al. | |
| 2008/0170749 | A1 | 7/2008 | Albertson et al. | |
| 2009/0005188 | A1 | 1/2009 | Iwatsubo et al. | |
| 2009/0017930 | A1 | 1/2009 | Burnett et al. | |
| 2011/0028248 | A1 | 2/2011 | Ueda | |
| 2011/0260890 | A1 * | 10/2011 | Larsen | A63B 69/3667 341/20 |
| 2012/0143358 | A1 * | 6/2012 | Adams | G06F 3/011 700/92 |
| 2012/0163675 | A1 * | 6/2012 | Joo | G06T 7/13 382/107 |

FOREIGN PATENT DOCUMENTS

| | | |
|---|---|---|
| WO | 96/16706 | 6/1996 |
| WO | 2004/042517 | 5/2004 |
| WO | 2005/005947 | 1/2005 |
| WO | 2005/094953 | 10/2005 |
| WO | 2006/120658 | 11/2006 |
| WO | 2009/060010 | 5/2009 |

OTHER PUBLICATIONS

PCT/EP2012/068008 ISR and Written Opinion, dated Mar. 4, 2013, 14 pages.

PCT/EP2012/068009 ISR and Written Opinion, dated Mar. 4, 2013, 14 pages.

PCT/EP2012/068010 ISR and Written Opinion, dated Mar. 5, 2013, 14 pages.

\* cited by examiner

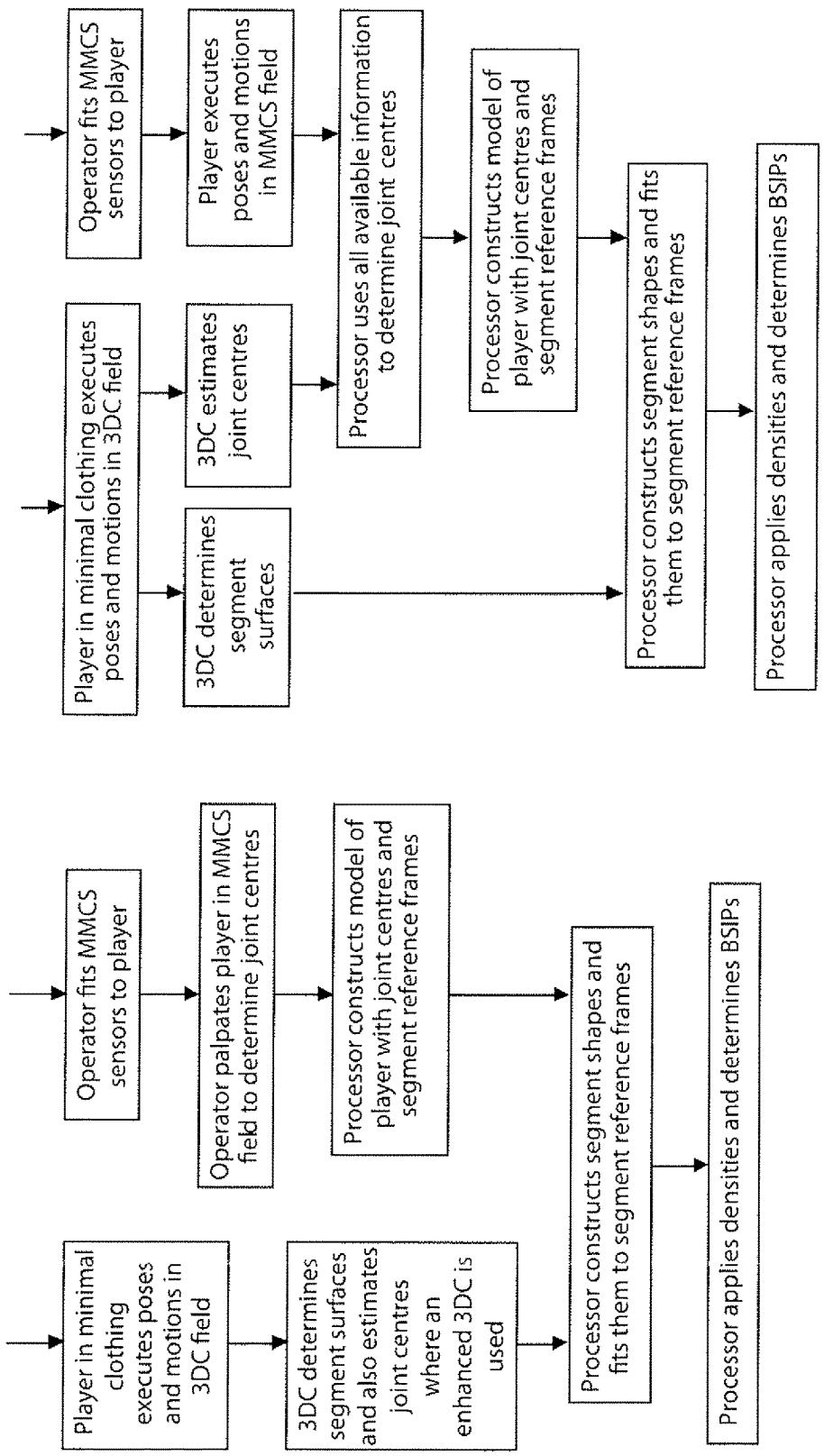

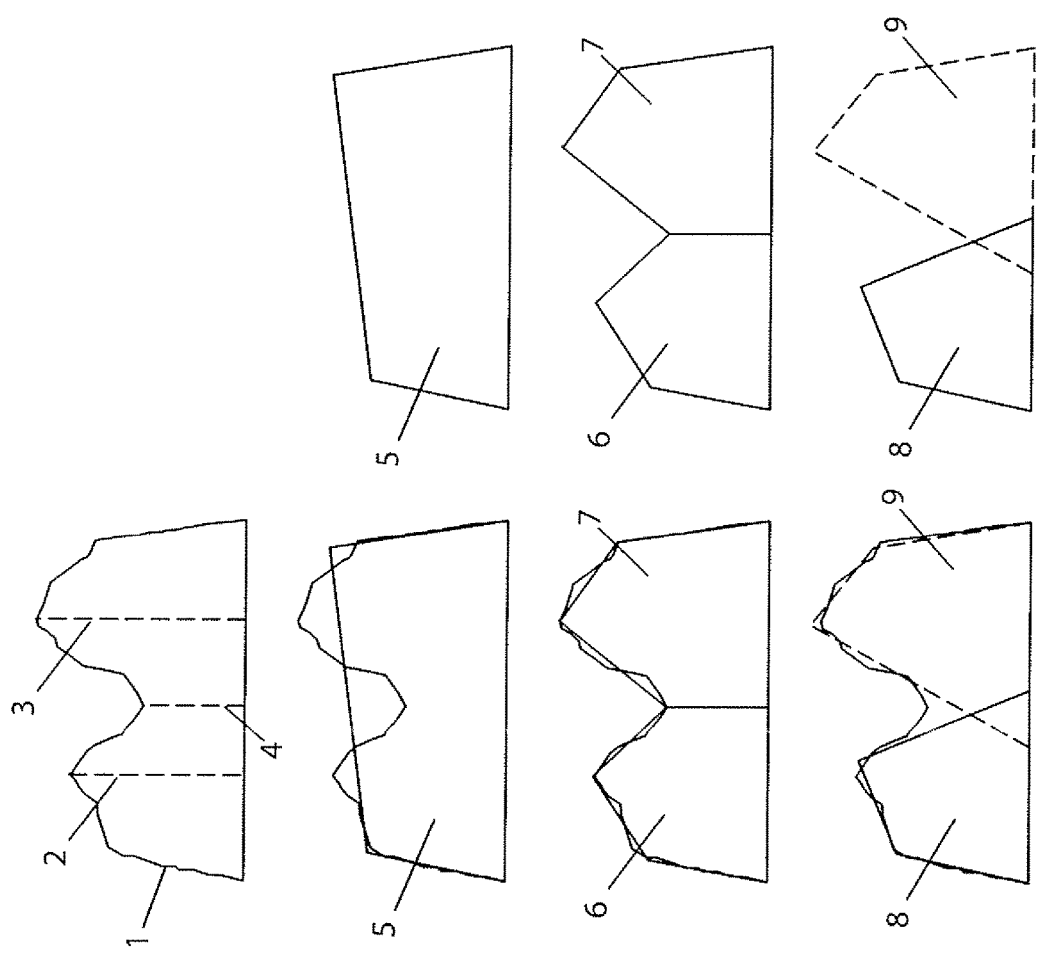

APPARATUS AND METHOD FOR ANALYZING A GOLF SWING

The present invention relates to an apparatus and method for measuring or analysing kinetic characteristics of a golf swing, including characteristics related to energy generation in a player's body and/or energy transferred through a player's body and club. The invention further relates to an apparatus and method involving measurement or analysis of energy generation or transfer in a chain of linked segments comprising the player and club. The invention relates more particularly to a system and apparatus where measurement and analysis are focused on the golf downswing and are used in coaching, or compilation of large databases used for coaching or analysis, where accuracy, cost and convenience are of importance.

The invention also relates to an apparatus and method which predicts kinetic characteristics of a golf swing, including characteristics related to energy generation in a player's body and/or energy transferred through a player's body and club, utilising a processor and artificial intelligence means, where parameters of the swing are measured with optical depth determination means and ground reaction force means, and the artificial intelligence means is trained with kinetic and kinematic information from a large database of golf swings.

The invention further relates to an apparatus and method which analyses kinetic characteristics of a golf swing, including characteristics related to energy generation in a player's body and/or energy transferred through a player's body and club, by converting complex energy related data into a format which extracts and communicates its essential features in a form which can be intuitively understood by a user or more easily processed by further apparatus.

U.S. Pat. No. 5,772,522 discloses a method and apparatus for analysing a golf swing where the golfer is modelled as a particular system of linked rigid body segments. A dynamic computer model of the golf club is combined with a computer model of the golfer. The models are kinematically driven from processed data derived by tracking markers on the golf club and golfer using an optical motion capture system. Although the method is primarily directed at providing analysis of the effects of changes in club parameters on the outcome of the swing, it also claims to provide analysis of the kinematics and kinetics of the golfer's body. The method is not capable of automatic operation, requiring, inter alia, adjustment through trial solutions with different parameters. There are various significant deficiencies in the modelling of the golfer. Some of these deficiencies entail artificial corrections to compensate for inflexibility in the model. One artificial correction involves making one arm rigid and another flexible to accommodate the looped system of the arms. Another artificial correction involves superimposing a torque control function to prevent the feet of the golfer model losing contact with the ground, using force plates which solely measure vertical forces. Another deficiency relates to the use of individual body segment mass, inertia and size characteristics derived from average values from the general population, selected exclusively on the basis of gender, weight and height. Further deficiencies arise from treating the hands and club grip as a single rigid segment and the upper trunk as a single rigid segment. Another deficiency arises from the evident location of lumbar and thorax joints at central positions on the trunk. The document makes no mention of numerous techniques and precaution which are necessary for providing meaningful analysis of the kinetics of the swing and makes no disclosure of specific techniques used in calculating force or power data from the model.

U.S. Pat. No. 7,318,779 also discloses a method and apparatus for analysing a golf swing where the golfer is modelled as a system of linked rigid body segments. Movement is captured with an active optical motion capture system. A digitising probe and static pose fixture, for holding the golfer in a static upright position, are used to obtain joint centre measurements and to position and orient markers relative to the golfer. Lengths of limb segments are also obtained from this process. Using the golfer's age, weight and height, a computer software package is used to build a golfer model based on average properties from a database within the software package, although no disclosure is made as to how this is carried out. When measuring motion, only positional data is collected, such that there appears to be no resolution of indeterminacies of forces in the closed loops of the legs and arms. The document suggests that inverse dynamics be used to determine joint torques, but no disclosure is made of techniques used in calculating these parameters.

U.S. Pat. No. 5,625,577 once again discloses a method and apparatus for analysing a motion such as a golf swing where the golfer is modelled as a system of linked rigid body segments. The method is claimed to be capable of displaying and analysing a swing, in various formats including an animated form on a computer screen, without requiring trial and error or the intuition of an analyst. The golfer is modelled with jointed segments and a database is maintained of physical constraints and inherent properties of body segments. The motion is recorded and individual segment motions are analysed using inverse dynamics. The motion is then adjusted by translations and rotations until the physical constraints from the database are met. Inverse dynamics are then reapplied to obtain an integrated set of results. The golfer model comprises about fifty body segments and the inverse dynamics calculations are commenced at the ground and carried through to the arms and head. Body segments are approximated by polygons. Similar to the previously discussed document, when measuring motion, only positional data is collected, such that there again appears to be no resolution of indeterminacies of forces in the closed loops of the legs and arms. No details are given of apparatus other than that a computer is used and motion may be recorded using video tape.

None of these prior art documents discloses a system for measuring a golf swing, using calculation techniques such as inverse dynamics, which can be practically applied to measuring swings of individual golfers and are thus unsuited for practical golf coaching purposes.

WO 2009/060011 discloses a method and apparatus for analysing a golf swing where the golfer and club are treated as a system of linked rigid body segments through which energy is generated and transferred to the clubhead. Data is obtained from the golfer's ground-reaction forces and processed signals are analysed with an artificial intelligence means trained with data obtained from other measurement and analysis systems. The system does not utilise inverse dynamics or similar techniques, and does not involve determination of body segment inertial parameters or address issues of indeterminacies at the closed loops of the legs and arms in the linked chain of segments. The accuracy of the system is dependent on the accuracy of data used in training the artificial intelligence means.

STATEMENTS OF INVENTION

The present invention is particularly defined in the appended method and apparatus claims which are incorporated into this description by reference and for the purposes of economy of presentation are not reproduced in the description.

The term "analysing" as used in the description and claims, includes measuring and/or analysing and should be construed accordingly. The term "determining" as used in this description and claims, includes measuring and/or determining and should be construed accordingly.

DESCRIPTION OF AN EMBODIMENT OF THE INVENTION

The measurement and analysis of human movement is made difficult by its variability and underlying complexity. This is particularly the case for a rapidly executed, skilled movement, such as the golf swing. Without limitation to its scope, the invention shall be described with reference to the golf downswing. The golf downswing presents particular measurement and analysis difficulties, including execution at high speed with high levels of acceleration and involvement of the entire body in addition to the golf club.

An aspect of the invention relates to a realisation that key approaches to analysing the golf swing include focusing on kinetic characteristics and the period of primary energy generation and transmission comprising the downswing. Analysis of kinetic characteristics presents various difficulties. One of these relates to accurately attributing movement to specific individual muscles from the highly complex muscle system of the body. In an example which shall now be described, this potential difficulty is overcome by attributing movement to muscle groups associated with specific joints of the body. This simplification has the additional advantage of facilitating communication of results to players and coaches. Throughout this document, the term "player", rather than "golfer", is used to generally represent a golfer or any person who executes a golf swing. In the analysis related to muscle groups associated with joints, particular attention is given to the analysis of the kinetic parameters of net joint torque, net joint force, their time derivatives of joint work and joint power, together with the relative values, timing, patterns and sequences in which they occur. These will be collectively referred to as 'net joint parameters' or 'NJP's. 'Net joint force' refers to the resultant of the forces acting through the joint. Similarly, 'net joint moment' refers to the resultant of the moments created by the muscle group acting at the joint about the joint centre. 'Net joint work' at any joint is given by the product of the net joint torque and the angular displacement and 'net joint power' or 'joint power' is given by the product of the net joint torque and the angular velocity of the joint.

System for Determining Kinetic Parameters

The kinetic parameters of some relatively slow and low acceleration simplified human movements, or part body movements, have been measured with varying degrees of success in prior art with techniques using muscle electromyography, force plates, and instrumented clubs. However, these techniques have been unable to measure anything more that a few very limited NJPs in the golf downswing, and these usually under difficult and restrained laboratory conditions. Other techniques using principles of dynamics, including inverse dynamics and forward dynamics, have also been attempted, but entirely without practical success in relation to full body fast motions with high accelerations where the requirements include sufficient accuracy and convenience to allow them be used for practical coaching, training or large database compilation.

Inverse dynamics calculates the net forces and moments across the joints of a body system, necessary to produce the observed or measured motions of the joint. The body system is of the type comprising chains of freely jointed rigid or substantially rigid segments. The calculations are carried out step-by-step through the chain of connected segments. Typically, Newton's equation of force, relating mass and linear acceleration, is used to derive linear accelerations of the centres of mass, and Euler's equation relating moment of inertia and angular acceleration, is used to derive angular accelerations about the centres of mass. However, it appears that practical measurement of NJP's, with levels of accuracy sufficient to be of use in meaningful coaching, training, compilation of significantly sized databases, or gathering of enough results to allow meaningful analysis of the general golf swing, has never been successfully achieved in a full body golf downswing in prior art, whether using principles of inverse dynamics or any other means.

Numerous difficulties arise in applying inverse dynamics to the fast moving golf downswing, many of which are not obvious to foresee. One difficulty arises in that calculation errors occurring in one segment can be carried along and multiplied in the calculations of further segments along the chain of linked body segments. Another difficulty arises in relation to indeterminacies with respect to forces in the legs and at the feet. A further difficulty relates to indeterminacies in calculations across the closed kinematic chain at the junctions of the left and right arm segment chains. Another difficulty arises from the assumption that body segments are rigid and that their relevant parameters remain valid through the movement. In reality, segments are not rigid, and the techniques used must minimise errors resulting from this simplification. A further difficulty relates to obtaining accurate measurement of the kinematic parameters of all segments through the swing. These measurements are complicated by the high speed movement of the downswing, where joint positions are never directly visible and external surfaces of segments are frequently occluded or vary their positions relative to other parts of the segment. Another difficulty arises from step disturbances from impact between the club and ball. A further difficulty arises from the typically noisy characteristics of signals from motion capture systems, where errors are magnified when displacement information is differentiated and double differentiated to obtain velocity and acceleration parameters. An additional difficulty arises from the need to obtain measurements in a manner which is sufficiently fast and cost effective for the needs of coaching and training and which allows the player execute the movement in a manner that is representative of real play. Similarly, the need to obtain measurements in a manner which is fast and cost effective arises with database collection, or gathering of sufficient data to allow general analysis of the swing. All of these difficulties are identified and overcome in the present invention, which comprises a very particular combination of appropriate and improved cost-effective systems and techniques involving measurement of body parameters, ground reaction forces, and calculations of other relevant external forces, together with appropriate and improved systems and techniques for measurement of kinematic parameters and application of inverse dynamics.

In the present example the player and golf club are modelled as a linked system of simple universal rotational joints and substantially rigid body segments. Although various arrangements of human segmented models are known in prior art, all have been found to have numerous deficiencies when tasked with accurate modelling of the golf swing. These deficiencies are overcome in the present invention.

The player's body segments comprise left foot, left lower leg, left upper leg, right foot, right lower leg, right upper leg, pelvis, middle trunk, mid-upper trunk, head, left upper trunk, left upper arm, left lower arm, left hand, right upper trunk, right upper arm, right lower arm and right hand. The joints comprise left ankle, left knee, left hip, right ankle, right knee, right hip, lumbar, thorax, neck, left inner shoulder, left outer shoulder, left elbow, left wrist, right inner shoulder, right outer shoulder, right elbow, right wrist and grip between the hands and club. Potential joints between the toes and those parts of the feet between toes and ankles are disregarded on the basis that they contribute insignificantly to energy generation in the golf downswing. A potential joint between the head and neck is also disregarded on the same basis.

Although the spine comprises multiple joints between individual vertebrae, it is found advantageous to represent the movement by a small number of joints. Three specific joint positions along the spine in the lumbar, thorax and neck regions are used in the present example. The height of the joint in the lumbar region is defined by the external anatomical landmark of height of the iliac crests, which approximates to the height of the division between the fifth lumbar vertebra and sacrum, L5-S1, where height refers to the player in an upright standing position. The height of the joint in the thorax region is defined by the external anatomical landmark being the height of the xiphoid process, or base of the breast bone, which approximates to the height of the eighth thoracic vertebra, T8. The joint in the neck region is defined by the height of a line passing through the external anatomical markers of the sternal notch and the seventh cervical vertebra, C7. Greater numbers of joints may be used to increase the accuracy of the model, the choice being a balance between accuracy and increased complexity in the analysis results and measurement equipment.

In the anterior posterior direction, the joints in the lumbar and thorax regions are positioned at points lying between the centres of the vertebrae and a small distance forward in the anterior direction, up to about one quarter of the distance from the rear to the front of the trunk. This recognises the relative inflexibility of the spine which largely determines the pivoting motion of the trunk. The joint may be located a little forward of the spine in recognition that flexing can occur at every vertebra and the greater part of the trunk, positioned forward of the spine, also has some influence on its movement. This rear positioning of the lumbar and thorax joints is usually not present in prior art models comprising jointed segments, where the joints are typically positioned, in the anterior posterior direction, at the centre of the trunk, giving rise to very significant moment of inertia errors in relatively fast rotational movements such as the golf swing.

In conventional biomechanics, the boundaries of adjacent segments are always constructed to lie on different sides of the joint connecting those segments. However, tests have shown that although this usually provides a satisfactory result, it does not always present the optimum solution. Optimum position joints can be found from techniques described later in the description, including techniques referred to as common-centre and locked-common-centre techniques.

The 'grip' joint corresponds to the joint between the hands and the proximal region of the club shaft. It has been found that significant movement occurs between the hands and club shaft during the downswing, involving generation of energy. The grip joint is complex and may be successfully modelled as one pivoting about a point between the left and right hands, positioned on or close to the central axis of the club shaft. In the calculations for driver clubs, the pivot point may, for example, be taken as a point on the central axis of the shaft about 12 cm down from the proximal end of the shaft. Throughout the specification, the term 'distal' refers to directions along the player's body and attached club, directed towards the clubhead or the player's head, and the term 'proximal' refers to opposite directions along the player's body directed towards the contact between the player's left or right feet and the ground.

Segment shapes of prior art models typically have little regard to actual movement which takes place across the joint which can lead to significant errors with portions of the body being ascribed to incorrect segments. This particularly applies to the hip and shoulder joints, where prior art limb segments are invariably modelled as substantially symmetrical shapes about central axes where they adjoin the trunk. Where possible, this is avoided in the present examples, where adjoining limb and trunk segments are approximately matched to notional movement planes.

Tests have shown that the shoulder cannot be accurately modelled with a single rotational joint between the upper trunk and upper arm. Accordingly, the upper trunk is divided into three segments, referred to as the mid-upper trunk, left upper trunk and right upper trunk. The left upper trunk connects to the left upper arm with the left outer shoulder joint and to the mid-upper trunk with the left inner shoulder joint. Similarly, the right upper trunk connects to the right upper arm with the right outer shoulder joint and to the mid-upper trunk with the right inner shoulder joint.

Anatomically, the shoulder joint group is complex and does not present an unambiguous division of segments in its composition. An aspect of the invention involves a recognition that expected errors in setting the division between the mid-upper trunk segment and the left and right upper trunk segments have fortuitously little effect on the overall accuracy of the inverse dynamics calculations because the inertial effects of relative movement between the segments is relatively small, even though the power generated across these joints is significant.

Figure 1:
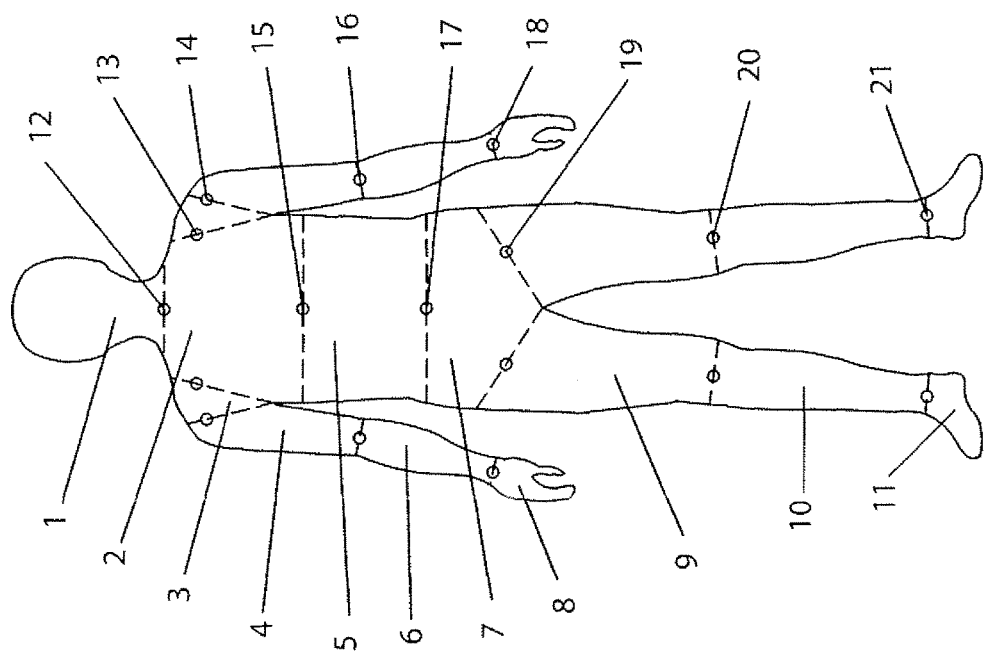

FIG. 1 shows an example of body segments and joints used in a model with inner and outer shoulder segments and where segments boundaries between the trunk and upper arms and upper legs are angled to approximate to notional movement planes of the joint. Segment boundaries are indicated by dashed lines and joints are indicated by small circles. An index of reference numerals used in the figure is shown below. For clarity, reference numerals for segments on the left side and joints on the right side are omitted in the figure.

1. Head (segment)
2. Mid-upper trunk (segment)
3. Right upper trunk (segment)
4. Upper arm (segment)
5. Middle trunk (segment)
6. Lower arm (segment)
7. Pelvis (segment)
8. Right hand (segment)
9. Right upper leg (segment)
10. Right lower leg (segment)
11. Right foot (segment)
12. Neck (joint)
13. Left inner shoulder (joint)
14. Left outer shoulder (joint)
15. Thorax (joint)
16. Left elbow (joint)

17. Lumbar (joint)
18. Left wrist (joint)
19. Left hip (joint)
20. Left knee (joint)
21. Left ankle (joint)

In the present example, NJPs are calculated using techniques of inverse dynamics described over the following paragraphs. The measurement inputs comprise three dimensional (3D) data related to the positions of the player's body segments and ground reaction forces acting at the player's left and right feet, over the course of the downswing. They also comprise 3D data on the characteristics of the player's body segments, referred to as 'body segment inertial parameters' which shall henceforth be abbreviated to 'BSIP's. For each segment, these BSIPs include joint positions, mass, mass distribution or centres of mass and moments of inertia in each of the principal mutually orthogonal directions.

Four segment-by-segment Newton-Euler calculations are commenced from four extremities of the player and club model, these extremities being the ground contact point of the left foot, the ground contact point of the right foot, the distal region of the club and the distal region of the player's head. The segment-by-segment calculations usually terminate at the lumbar and thorax joints, ideally with calculations being made from both directions at each of these joints, such that values from proximal-to-distal and distal-to-proximal are obtained at both joints. The lumbar joint is positioned between the pelvis and middle trunk segments and the thorax joint is positioned between the mid-upper trunk and middle trunk segments. The values used in the inverse dynamics calculations at the lumbar and thorax joints is decided by choosing that which is expected to be more accurate and reliable in the distal-to-proximal or proximal-to-distal calculations, as relative levels of accuracy and reliability can vary for different apparatus.

The forces and moments at the first joint in the chain commencing with the left foot, at the left ankle joint, are found from the 3D combination of ground reaction forces, which for brevity will henceforth be referred to as GRFs, at the proximal end of the left foot together with gravitational forces and inertial forces arising from movement of the foot as detected by kinematic measurements of movement of the foot. Inertial forces are found by applying the relevant foot segment acceleration and relevant foot BSIPs to the calculations. The gravitational force is calculated from the mass and centre of mass position, determined from the mass distribution. The joint-by-joint calculation then proceeds in a distal direction from the left ankle to the left knee and then to the left hip. A similar set of calculations is carried out from the proximal end of the right foot, using separately measured GRFs for that foot. The two sets of calculations converge at the pelvis segment allowing calculation of moments and force vectors at the lumbar joint by a process of appropriate addition. The joint-by-joint calculation is continued in a distal direction to the lumbar and thorax joints.

Apart from forces due to air drag and gravity, the net sum of applied forces and moments at the distal end of the club is zero, because the distal end moves without external constraint. Air drag forces are significant for club segments because of their relatively high speeds, and are appropriately accounted. Air drag forces are relatively insignificant for most segments of the player's body and in most cases need not be accounted. Where a high degree of accuracy is required, allowance may advantageously be made for air drag forces on the hands and arms, particularly the lower arms. Gravity forces should be accounted in all segments.

The joint-by-joint calculation from the distal region of the club proceeds in a proximal direction and splits into two paths at the grip joint to the left and right hands. This gives rise to potential indeterminacy in the division of forces and moments which cannot be accurately resolved by the inverse dynamics calculation alone.

The division cannot be estimated by resorting to prior art information on the subject because it appears that no means has previously been found to properly determine joint powers in the joints of the right and left arms during a swing, and it seems that the relative proportions of work done by the left and right arms has hitherto been completely unknown.

This problem is solved in the present invention. The division is measured using an instrumented club which is operable to measure forces between those two portions of the club shaft gripped separately by the left and right hands. The relevant forces comprise the constantly changing resultant forces and moments at the point of division between the two portions across the downswing. These forces are measured independently of the swing or, alternatively, are measured alongside general measurement of the swing.

The joint-by-joint calculation from the left hand continues in a proximal direction to the left wrist, left elbow, left outer shoulder and left inner shoulder joints. A similar set of calculations is carried out from the right hand. A set of calculations also proceeds from the head segment in a proximal direction to the neck. Apart from gravity and air drag forces, the forces and moments at the distal region of the head are similarly zero, because the head also moves without external constraint. The three sets of calculations, from the left hand, right hand and head, converge at the mid-upper trunk segment, allowing calculation of moments and force vectors at the thorax joint by a process of appropriate addition.

The calculations continue from the thorax joint to the lumbar joint. Thus calculated values are obtained for the lumbar and thorax joints from both directions. In an ideal situation where high quality data is obtained from the motion capture and force plate systems, the proximal-to-distal value is used for calculating NJPs at the lumbar joint, the distal-to-proximal value is used for calculating NJPs at the thorax joint and the second value for each joint is used as a monitoring check. The reason for this is to minimise the influence of the middle trunk segment in the calculations. The middle trunk presents the greatest difficulties in estimating segment parameters because it is the most difficult of the large segments for accurate estimation of density and centre of mass. Density estimation is complicated by the presence of the lung cavities. Centre of mass estimation is complicated by its relatively high mobility due to breathing and presence of relatively large amounts of flexible soft tissue. The segment typically changes shape as the player moves or bends forward. Normally, all joints distal to the thorax joint use distal-to-proximal values for calculating NJPs and all joints proximal to the lumbar joint use proximal-to-distal values for calculating NJPs.

However, where a particular system is found to have significantly better quality proximal-to-distal or distal-to-proximal data up to points on the chain other than as indicated above, the better quality data should normally be used. If distal-to proximal data is found to be of better quality at all segments, it may be used for all segments and the ground reaction forces used just to establish the division of forces between the pelvis and upper leg segments. In the instance of the present example, optimum results have been found using distal-to-proximal calculated values for the thorax joint and proximal-to-distal calculated values for the lumbar joint.

FIG. 2 shows a diagram depicting the routing of inverse dynamics calculations in the example of inverse dynamics calculations described above, where the calculations are terminated at the lumbar or thorax joints. The abbreviations 'IDCPDF' and 'IDCPPF' in the diagram signify 'inverse dynamics calculations proceed distally from' and 'inverse dynamics calculations proceed proximally from', respectively.

Apparatus for Determining Kinetic Parameters.

An example of an apparatus for determining NJPs shall now be described, which is suitable, inter alia, for use for individual coaching and compilation of large databases used for coaching or analysis, where cost and convenience are important. The apparatus is also suited for ready transfer and set-up at different sites, where such is required. The apparatus may also be used to determine and analyse other aspects of golf swings, including kinematic aspects, which are not discussed in detail in this specification. In addition to their direct use in coaching and practice, kinematic parameters are also used in calculating segment kinetic energy parameters, which, inter alia, are used in calculating transfer of generated energy.

The apparatus comprises means for tracking and measuring a player's joint positions and GRFs over the course of a downswing and for measuring the player's BSIPs. The data is processed in a processing means and results in various formats communicated to a user by a communication means. The user may be a coach, player or operator or may comprise other apparatus or systems.

The common method for capturing complex or high-speed kinematic movement with high accuracy is to use an optical motion capture system employing several high speed cameras which capture the movements of strategically placed passive markers on the subject. However, such systems can be unreliable and inaccurate in measuring the 3D position of closely positioned points on a moving surface because they constantly need to be able to unambiguously distinguish and view at least three optical passive markers for each point measured. Markers are frequently occluded during player movement and particular difficulties can be encountered in accurately tracking the movement of closely spaced points on the player's spine during the golf downswing. High speed optical systems also typically require lengthy set-up and a large indoor laboratory type space. They are also usually incapable of operating in real time, which, in addition to losing the advantages of having feedback available during a coaching session, prevents immediate detection of faulty results which would otherwise allow retesting to be conveniently carried out while the player and setup remain available.

Magnetic motion capture systems, sometimes referred to as electromagnetic motion capture systems, overcome the problems of marker occlusion and are available in several formats, including wired and wireless types, and AC and pulsed DC types. They typically produce less noisy output signals than optical systems. They tend to be less favoured in prior art studies of human movement for several reasons. One of these reasons is that they require active sensors attached to the player. Another reason is that attachment of sensors can be difficult, time consuming and prone to errors. A further reason is that the sensors are sensitive to signal distortion from the presence of certain electrically conducting materials, including the materials of other measurement apparatus. In relation to golf swing measurement, an additional reason is that it is impractical to mount active sensors on or close to the clubhead, and this prevents direct detection of clubhead position when determining the instants of takeaway and impact. All of these difficulties are successfully overcome in the system and apparatus of the present example. Tests have indicated wired AC types to be the most suited for accurate measurement of the downswing, with wireless and pulsed DC types having inadequate sampling speeds or inadequate levels of resolution and accuracy.

An example of a suitable wired AC magnetic motion capture system is given by the Polhemus Liberty™ system. In the present example, the player is fitted with active sensors at strategic points on the body and club, such that the positions and orientations of all segments are tracked through the swing in a reference magnetic field, sometimes referred to as an electromagnetic field, generated by a transmitter. Each sensor tracks six degrees of freedom through the course of the downswing, these comprising positions and angular orientations about each of the three mutually orthogonal axes of the reference field. The motion tracker system provides real time movement data at a typical update rate of 240 Hz, a static accuracy position of around 0.03 in and static accuracy orientation of around 0.15° RMS.

The following arrangement, with twelve sensors, can be successfully used with the eighteen segment player body model, comprising left foot, left lower leg, left upper leg, right foot, right lower leg, right upper leg, pelvis, middle trunk, mid-upper trunk, head, left upper trunk, left upper arm, left lower arm, left hand, right upper trunk, right upper arm, right lower arm and right hand. Sensors are attached at the upper rear region of the left lower leg, rear of the left upper leg, upper rear region of the right lower leg, rear of the right upper leg, one side of the pelvis, rear of the middle trunk close to vertebra position T12, rear of the mid-upper trunk close to vertebra position T8, rear of the left upper arm, rear of the right upper arm, back of the left hand, back of the right hand and at the side of the player's head. An additional sensor is attached at the front upper part of the club shaft below the hand grip of the club.

Each lower arm is tracked by the hand sensor tracking the wrist joint and the upper arm sensor tracking the elbow joint. The overall movement of the lower arm segment is estimated by appropriate software algorithms based on knowledge of typical lower arm movement following the positions and orientations of the wrist and elbow joints. This algorithm takes account of the characteristic of the lower arm whereby simple rotation about its long axis does not occur about the elbow, but a more complex form of rotation occurs about a region significantly further along the lower arm. With the types of suitable sensors currently available, omitting lower arm sensors has the advantage of reducing cost, complexity and encumbrance of the player by additional sensors and wires on these relatively fast moving segments. If suitable less obtrusive or wireless sensors become available at a future date, it may become advantageous to position sensors on each of the lower arms to increase tracking accuracy.

The usual prior art method for attaching sensors to a human subject in a biomechanics laboratory type environment is to arrange for the subject to wear minimal clothing and to adhesively tape all of the sensors, other than the head sensor, directly to the skin. This is commonly believed to be essentially for accurate identification of anatomical marker positions and to ensure that sensors remain in place during testing. However, this method is unsuited for individuals such as golf players undergoing testing or coaching, who are unaccustomed to biomechanics test procedures. It is unpleasant and time consuming for the player and expensive in relation to apparatus facilities and the test operator's time. A system is disclosed which overcomes these problems and includes attachment of sensors with special-purpose, adjustable straps, harnesses or jackets, details of which are given later in the description. Tests have shown that this system gives comparable levels of accuracy to the prior art method.

As previously mentioned, magnetic motion capture systems have the relative disadvantage of being susceptible to problematic interference from magnetic-related materials within the local environment. In the case of an AC system, such materials particularly refer to moderate amounts of high conductivity metals including copper, aluminium, brass and some types of steel and iron, or to large or closely adjacent amounts of any metal. This creates the potential for difficulty in measuring the golf downswing because golf clubs and measuring apparatus, such as force plates, typically contain such problematic metals. Problematic metals may also be present in beams or internal reinforcing bars in floors and ceilings. Problems from such metals are overcome in the present invention by various means.

Potential difficulties with stationary problematic metals, such as adjacent steel beams or internal reinforcing bars in ceilings or floors, are dealt with in two principal ways. First, where possible a test area is chosen with minimal problematic metals. Second, light to moderate distortion is corrected using compensating mapping software which may be available from the supplier of the motion capture system. The mapping process typically involves moving a fixture systematically through the 3D space to be mapped such that the levels of position and orientation distortion are measured throughout the 3D space. The fixture may comprise a vertical non-conducting pole with evenly spaced sensors positioned along it. The data is entered in the mapping software to compute a correction algorithm that is used by the motion tracking system.

The mapping process may be found to be inadequate for sensors which move close to large amounts or areas of problematic metals. This is likely to arise with sensors located on the feet where the player stands on a force plate with a metal platform. This problem can be solved in different ways. The solution used in the present example is to omit sensors from the feet and to track the positions and orientations of the ankles by sensors positioned on the upper region of the lower leg segments. These sensors are positioned at heights sufficient to avoid significant distortion from the force plates. With this solution, the feet are assumed to remain in contact with the surface of the force plates, and their positions are estimated by appropriate software algorithms based on the positions of the ankles, the player and the centres-of-pressure of the feet on each force plate, combined with knowledge of typical foot positions through the downswing. Errors arising from this estimation are small due to the relatively small movements and low speeds of the feet in the downswing. Alternative arrangements may be required where it is also necessary to accurately track the kinematic movement of the player in the backswing and follow-through, where the feet are frequently lifted and turned in ways which are more difficult to predict solely from movement of the ankle. This may be achieved in various ways. For example, the player may stand on rigid non-metallic platforms positioned on the force plates, distancing the sensors from the force plates. GRFs can be successfully transmitted to the force plates using this method. In another example, the sensors are mounted on non-metallic rigid supports attached to each of the shoes of the player, close to the ankle end, keeping the sensor sufficiently above the level of the force plates. In a further example, a force plate with non-conducting components may be used. Such force plates are available but are relatively expensive.

Solutions must also be found for problematic metals which are not stationary in the 3D space. In particular, difficulties can arise with distortion of signals from sensors attached to metal club shafts. In the present example, this problem is overcome with metal shafts by clipping the sensor to the shaft using a non-metallic arm which positions it a short distance away from the shaft. Alternatively, clubs can be used with non-metallic shafts, but this may preclude players from using their own clubs or clubs with characteristics familiar to them.

Figure 3:
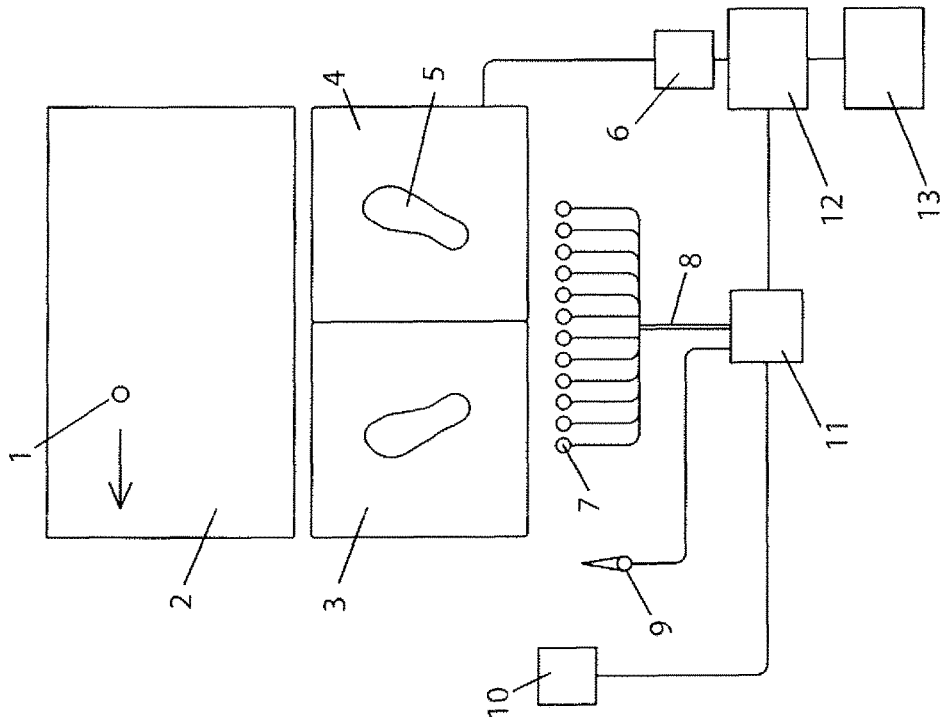

FIG. 3 shows a schematic plan view of an example of apparatus for measuring kinematic and GRF parameters in a golf swing. An index of reference numerals used in the figure is shown below. The abbreviation 'MMCS' refers to magnetic motion capture system.

1. Ball in tee or starting position. The ball is hit in the direction of the arrow.
2. Artificial playing surface.
3. Left foot force plate.
4. Right foot force plate.
5. Player, represented by outline of feet.
6. Processing and interface unit for force plates.
7. MMCS sensors, fixed to player segments and club shaft.
8. Umbilical connection of wires from sensors to MMCS processing and interface unit.
9. MMCS stylus.
10. MMCS magnetic field transmitter.
11. MMCS processing and interface unit
12. Apparatus processor.
13. Operator interface.

Referring to FIG. 3, the player stands on the force plates and hits the ball in the direction shown by the arrow. Although not shown in the figure, the MMCS sensors are fixed to player segments and the club shaft, as described elsewhere. The force plates and MMCS record GRF and kinematic parameters, which are processed by their respective processing and interface units, and are passed to the apparatus processor. The test operator controls and monitors the system through the operator interface. The MMCS magnetic field transmitter is located in an elevated position, close to the sensors but out of reach of the movement of the player and club. Although shown to one side of the player in the figure, in reality it is located behind the player to be as close to the sensors as possible. The MMCS stylus sensor is used to measure parameters related to the player's BSIPs within the reference frame of the MMCS. Where metallic force plates are used, the player will usually move a distance from them when these parameters are measured.

The division of forces in the arm loop is determined using an instrumented club which calculates the relevant forces or division of forces at the grip joint over the course of a swing. The instrumented club may comprehensively measure forces in three dimensions at the grip joint, or may be simplified to measure a narrow relevant selection of the forces, for example simple bending moments at the grip joint. Where comprehensive 3D forces are measured, these can be used directly in the inverse dynamics calculations, as they represent the complete distal forces acting at the grip joint. Where simple bending moments alone are measured, these can be used to estimate the division of forces at the grip joint by providing an additional input to solve indeterminacy of forces in the arm loop. An improved estimate is obtained where both bending moments and torsion are measured at the grip joint.

Although an instrumented club could be used for all swings, this is not done in the present example because the instrumented club is encumbranced with additional wires and is less realistic in use than a normal club. Also, it would add further complication to data collection during routine testing. In the present example, the player separately executes one or more swings with an instrumented club of similar type to the club used for inverse dynamics calculation. The force profiles over the course of the swing are measured and recorded. These profiles are then applied to all swings for that type of club by that player, up to such time as the profiles are measured again and updated.

The profiles are tagged against swing angular position to allow them be correctly synchronised with test swings. Tagging may be carried out, for example, by using the motion capture system alongside the instrumented club. Alternatively, tagging may be carried out by matching and comparing the profiles to similar sample profiles which have been tagged with a motion capture system. This can be carried out automatically using an appropriately programmed processor.

A variation in this method involves measuring the grip force division for a representative number of players and applying the averaged results to players being tested. Player characteristics, such as level of skill and morphology, may be taken into account when applying results from samples of pre-tested players.

In one particular example, the instrumented club is constructed by attaching strain gauges to the outer or inner surface of the club shaft, around the diameter of shaft at the axial level of the grip joint. The strain gauges are arranged in a conventional balanced bridge arrangement and are positioned appropriately for the particular forces being measured, with gauges measuring bending moment aligned with the long axis of the shaft and gauges measuring torsion aligned at 45° to the long axis of the shaft. The gauges are conventionally calibrated and the grip region is re-covered with standard grip material, such that the gauges and wires are not obtrusively perceptible to the player. The strain gauges are connected to the system processor by wires routed from the proximal end of the club along the player's target-side arm, which is normally the left arm for right-handed players. In a second example, the instrumented club is constructed by dividing a standard club at the grip point, between the left hand and right hand grip portions, and rejoining both parts with an elongate metal member comprising flat areas where strain gauges are attached.

The instrumented club may comprise an instrumented shaft grip portion which can be fixed to a wide range of clubs, possibly connected by a screwed joint between the shaft grip portion and the remainder of the shaft and the clubhead.

Figure 4:
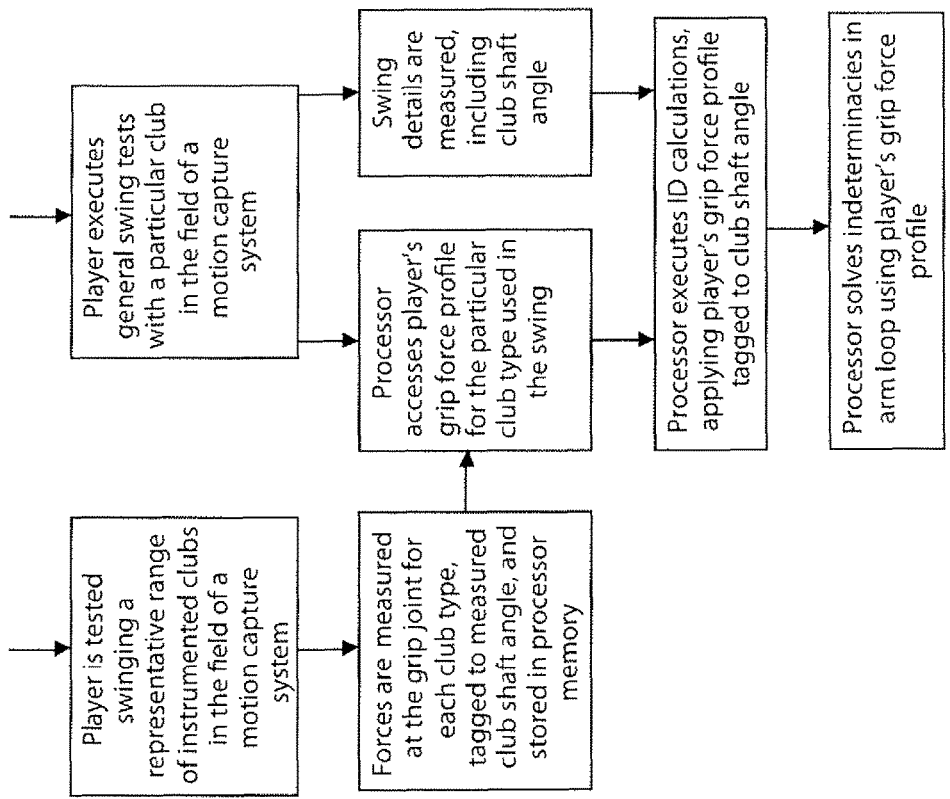

FIG. 4 shows a diagram depicting some of the steps involved where these techniques are used to apply a pre-tested grip force profile to solve indeterminacy in the loop of the left and right arms in inverse dynamics calculations. The abbreviation 'ID' refers to 'inverse dynamics'.

Throughout the description and claims, where reference is made to actions by a processor, these should normally be understood to mean actions by a processor using software. It should also be understood that appropriate and relevant algorithms are used within the software where required, although these will not usually be specifically stated and explained unless the required algorithm is one that would not be capable of implementation by those skilled in the art. Also, where a reference is made to a processor or system processor, this should normally be understood to refer to one or a plurality of processors, and to processors located within the apparatus or located remotely from the apparatus, since processors commonly communicate remotely. Where reference is made to data being available to a processor or system, this may refer to data being available from memory means within the processor or memory means accessible from a remote location. It may also refer to data which is not held in memory, but is accessible in other ways, including being calculated by a processor when requested. It may also refer to data which is obtained from a database which is regularly changed or updated.

In contrast with the player model, the golf club has been the subject of prior art development activity due to its comparative mechanical simplicity and competitive commercial importance. Several club models are known in prior art. The following approach and model has been found satisfactory for use with the player models and inverse dynamics calculations used in the present examples. Players are tested with a limited variety of club types which adequately represent the range of clubs used by the great majority of players. The relevant physical and inertial properties of each club type are determined and each club type is subjected to a finite element analysis, using the finite element method, employing proprietary software packages which provide the relevant differential equations describing their 3D flexing behaviour under swing conditions. Each set of results is subjected to a once-off set of validation tests using high speed cameras and passive markers on the clubs, with calculated results being adjusted where necessary to match with test results. The resulting equations are easily implemented by the system processor for the relevant club type, where movement measured by the system motion capture sensor for each swing provides the principal basis for inputs to the equations. As previously mentioned, this sensor is positioned on the grip end of the shaft.

Figure 5:
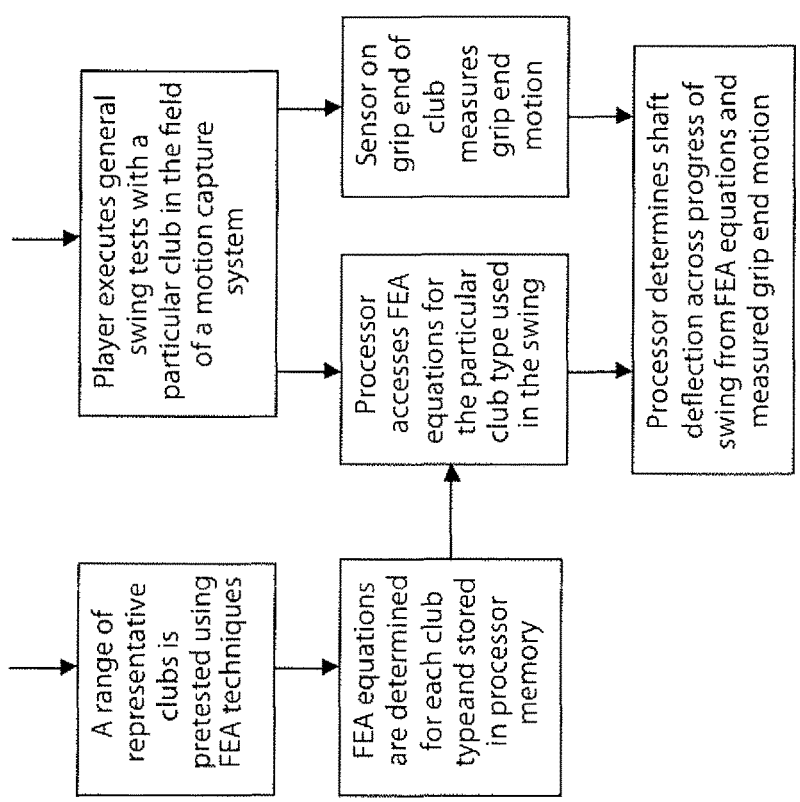

FIG. 5 shows a diagram depicting some of the steps involved where these techniques are used to determine club shaft deflection during a swing from measured grip end motion and pre-determined FEA equations for a club of the same type.

Inputs comprising data on GRFs of the player's left and right feet, over the course of the swing, are obtained using two side-by-side force plates. The force plates are of known square or rectangular type with strain gauge or piezoelectric transducers located under each corner of the standing platforms. The force plates are operable to measure GRFs on three mutually orthogonal axes, including vertical direction. Simpler single axis force plates, which just measure vertical forces, are not suitable where high accuracy measurement is required, because they do not account for the significant horizontal components of force which occur in the swing and will give rise to significant mismatch between proximal-to-distal and distal-to-proximal inverse dynamics calculations from the force plates and motion capture system. The player executes the golf swing, standing in a natural position with one foot on each force plate. Signals from the force plate sensors are fed to the processor where they are converted into required input signals describing the forces at each of the player's feet, including calculated centres of pressure which locate the point locations of the resultant forces. Analogue signals from the force plates are converted to digital format at a sampling rate which is synchronised with kinematic sampling but at a rate which is a multiple of the kinematic rate. For example, where the kinematic sampling rate is 240 Hz, the force plate signals may be sampled at 960 Hz.

Measurement of Body Segment Inertial Parameters

Inverse dynamic calculations require measurement of the player's BSIPs, which are conventionally assumed to be fixed in value. It is important that they are determined with a high level of accuracy and consistency, as errors in any segment which is not at the end of the linked chain will cause errors to be propagated from joint-to-joint along the chain of inverse dynamics calculations with multiplying effects on the results. Where the system is used for individual coaching or where a large database of players is being compiled, it is also important that BSIPs are measured with minimal inconvenience to the player.

In rigorous prior art biomechanical studies, BSIPs are typically measured by difficult and time consuming methods, including expensive non-contact scanning methods, inconvenient submersion methods or laborious one-off physical measurement and calculation. In less rigorous prior art biomechanical studies, to overcome these difficulties of time, expense and inconvenience, BSIPs are frequently derived from predetermined average values from some part of the general population, selected on the basis of anthropometric measures such as gender, age, body weight and overall height. The individual's segment parameters are estimated by applying regression equations based on the averages obtained from these samples taken from the population. However, tests have indicated this to provide a much less accurate and reliable basis of calculation, since, inter alia, the chosen part of the population usually will not accurately represent the subject and the regression equations will not account for individual body morphology differences. In practice, most data of this type appears to be invariably derived either from easily measured cadavers or readily available young athletic men and women, neither group representing the broad range of body shapes which typically occurs with golf players.

An aspect of the invention relates to an appreciation that errors in BSIPs affect inverse dynamic calculations quite differently for different types of motion. In particular, whereas errors in BSIPs initiate and propagate proportionally low and often tolerable errors in calculated forces and torques in the types of relatively slow simple movements where inverse dynamics calculations have been applied with some limited success, they initiate and propagate proportionately higher and much more serious errors in fast movements with high rates of acceleration, such as the golf swing, and require an altogether different level of care in their calculation, particularly for the faster moving more distal segments.

The highest accuracy is required in the measurement of BSIPs in the fastest moving and most highly accelerating segment, which is the club in the golf swing. This is fortuitous because the club is particularly amenable to very accurate measurement, being an inanimate object with relatively limited variation in its characteristics. Advantage may be taken of this characteristic by testing with limited numbers of carefully premeasured representative clubs.

The problems occurring with prior art approaches are overcome in two alternative examples, one based on palpation and the other based on use of a 3D camera system. The first of these will now be described.

In the palpated example, the shapes and volumes of body segments are calculated from simplified geometric representations of the segments, defined by specific anthropometric measured landmarks on the segment boundaries. Particular care is taken in modelling the middle and upper trunk segments, which comprise the greatest range of densities and are the least rigid of the body segments, other than the hands. Density estimates are used for each geometric solid, with solids comprising body cavities having lower densities than those without cavities. The 18 segment player body model, excluding the club, is subdivided into 28 geometric 'solids', which are defined by 89 measured anthropometric landmarks which are also used to define the joint centres. These geometric solids comprise truncated elliptical cones, semi-ellipsoids and ones which will be referred to as 'trunk solids'. When its principal axis is vertical, the trunk solid is symmetric about a central vertical front-to-back plane, with horizontal cross-sections comprising rectangles with semicircles at each end, the whole solid bounded by planes at the top and bottom and to the front and rear. The upper arm, lower arm, upper leg and lower leg segments are each sectioned into two truncated elliptical cones. The feet each comprise a truncated elliptical cone. Each hand comprises a trunk solid. The head comprises a semi-ellipsoid above a truncated elliptical cone. The mid-upper trunk, left upper trunk and right upper trunk form a group which shall be referred to as the 'upper trunk'. The upper trunk, middle trunk and pelvis comprise three, one and two trunk solids, respectively.

Most of the solids are defined by eight landmarks, four at each end defining the width and depth. Adjacent solids share landmarks, where practical. Where two solids of the central body, comprising the upper trunk, middle trunk and pelvis, meet with a common surface, the boundaries of the common surface are the same for both solids. Where two solids of the same geometric type within either arm or leg, meet each other with a common surface, the boundaries of the common surface are the same for both solids where the long axis of the solids, between joint centres, are collinear. Joint centres are calculated by geometric reference to two or more determined landmarks, which have some fixed reference to one of the adjacent segments comprising the joint centre. In the simplest method, the joint centres are estimated as the midpoint of a line constructed between lateral and medial points at the joints, known to be at the level of the joint. This has been found to give good levels of accuracy for ankle, knee, elbow and wrist joint centres. Similar simplified methods can be used for other joints, but using appropriate distances and offsets, rather than simple midpoints along lines, frequently using lateral, medial, anterior and posterior landmarks at or close to the level of the joint. Alternatively, estimates of joint centres can be obtained by use of regression equations, where the regression coefficients are predetermined from imaging techniques on representative samples of the population.

As described above, the truncated elliptical cones comprise elliptical frustums. However, a better solution is obtained by angling the surfaces of the truncated elliptical cones of the upper leg and upper arm segments, such that the hip and outer shoulder joints lie on the angled surface and the slope of the surface approximates a notional movement plane of the joint. Corresponding changes are made to the adjoining segments of the pelvis and middle trunk, matching the angle of the upper leg and upper arm segments. Although this angling of the surfaces reduces the simplicity of the moment of inertia calculations, it significantly increases the accuracy with which body mass is ascribed to correct segments in regions surrounding these joints.

A further particular difficulty is presented by the middle trunk segment, in that its centre of mass changes significantly when the player changes from an upright position, to a position leaning forward in the swing, with the extreme forward position typically occurring around the time of impact. The change in centre of mass is partly due to the compression of the relatively flexible middle trunk segment as the player bends forward, curving the spine, with trunk mass being prevented or inhibited from expanding to the rear due to being contained by the spine. The change in centre of mass is also due to the effects of gravity as the player leans forward and centrifugal force as the player rotates in the swing.

This change in centre of mass is accommodated in the present example by taking an additional set of BSIP measurements with the player in a typical leaning-forward position, such as the player's normal address position with a driver club. An additional centre of mass position is calculated from these measurements and the system processor automatically varies the middle trunk centre of mass position between the two centre of mass values using a routine written into the software, varying with swing angle. In an alternative simpler but less accurate arrangement, the centre of mass from a single appropriate leaning-forward position, or from an appropriate compromise between the upright and leaning-forward positions, is used and applied to all positions through the swing.

For each segment the mass, centre of mass location and principle moments of inertia are calculated by assuming a uniform density across each solid and applying appropriate specific density estimates, such as the following, to the volumes of each of these solids. Values of 1190 kg/m$^3$ and 1050 kg/m$^3$ are applied to the lower and upper leg solids. Values of 1130 kg/m$^3$ and 1070 kg/m$^3$ are applied to the lower and upper arm solids. Values of 1160 kg/m$^3$ are applied to the hands. Values of 1110 kg/m$^3$ are applied to the head and leg solids. Values of 1010 kg/m$^3$ are applied to the solids of the middle trunk and pelvis. Values of 1040 kg/m$^3$ and 1010 kg/m$^3$ are applied to the top and bottom solids of the upper trunk respectively. Values of 920 kg/m$^3$ are applied to the two middle solids of the upper trunk.

Various prior art methods have been used to carry out the physical measurement of landmarks, including the application of anthropometric callipers across segments. However, such methods can be time consuming and prone to error, because they must be applied in correct spatial relationship to other segment measurements and to some degree must be accurately tracked throughout the downswing. These potential difficulties are overcome in the present example by measuring the anthropometric landmarks with a 3D stylus digitiser, operating within the reference field of the magnetic motion capture system, with reference to one of the sensors of the motion tracking system which is in fixed relationship to the segment or joint.

The outputs from the stylus are recorded directly by the motion capture system in relation to the local coordinate system of the relevant sensor. The player, with body sensors attached, stands in an appropriate position within the magnetic field while an operator measures the player by moving the tip of the stylus to the landmark point. In the present system, for measurements other than those where the player specifically leans forward, this measurement position is with the player's head erect and looking forward, arms down but positioned slightly away from the sides with each hand in a first with the thumb facing forward and with feet parallel and apart. The stylus operates similarly to a sensor within the magnetic field and a processor associates the stylus points against a template within the software which calculates the various BSIPs. Although the player should ideally remain relaxed and still during palpation to assist the process, it will not unduly affect the results if he or she moves during measurement, because the sensors track the relative positions of the whole model.

The process is facilitated in several ways. The system comprises an audible communication means controlled by the system processor, which indicates landmarks, one-at-a-time by a name familiar to the operator, stepping through all landmarks to be measured. At each step the operator positions the tip of the stylus against the landmark and presses a button on the stylus. This causes the position to be recorded by the system and triggers the system to audibly signal the next landmark. The operator is trained in the accurate identification of the marker points by a process of observation and feeling with the fingers and hands, frequently termed 'palpation'. Tests have shown that particular care should be taken not to distort measurements of soft tissue by depressing the landmark point with the stylus. These various procedures promote rapid measurement and minimise the possibility of errors. Measurement time is further reduced by arranging the system to assume some degree of body symmetry in the player, such that geometric measurements of the central portions of the foot, lower leg, upper leg, upper arm, lower arm and hand segments on one side of the body are automatically applied to the other side. Separate landmarks defining the joints are however measured on both sides, ensuring inter alia that the relevant sensors accurate track the position and orientation of the corresponding segments.

The following is a list of the 90 anatomical landmarks used in the present embodiment for measuring male players, with a reference number shown in parentheses before the anatomical description of its position. A slightly modified version is used to more accurately measure female players, which includes additional anatomical landmarks which establish breast size. (1) Right foot Lateral Toe; (2) Right foot Middle Toe; (3) Right foot Medial Toe; (4) Right leg Lateral Malleolus; (5) Right leg Posterior Fibula; (6) Right leg Medial Malleolus; (7) Right leg Anterior Talus; (8) Right leg Lateral Maximal Calf; (9) Right leg Posterior Maximal Calf; (10) Right leg Medial Maximal Calf; (11) Right leg Anterior Maximal Calf; (12) Right leg Lateral Femoral Epicondyle; (13) Right leg Mid Popliteal Crease; (14) Right leg Medial Femoral Epicondyle; (15) Right leg Centre of Patella; (16) Right leg Lateral Mid Thigh; (17) Right leg Posterior Mid Thigh; (18) Right leg Medial Mid Thigh; (19) Right leg Anterior Mid Thigh; (20) Right leg Greater Trochanter; (21) Right leg Posterior Mid-Groin; (22) Right leg Anterior Mid-Groin; (23) Left foot Middle Toe; (24) Left leg Lateral Malleolus; (25) Left leg Left Medial Malleolus; (26) Left leg Lateral Femoral Epicondyle; (27) Left leg Medial Femoral Epicondyle; (28) Left leg Greater Trochanter; (29) Umbilicus; (30) Right Iliac Crest; (31) T12; (32) Left Iliac Crest; (33) RASIS (right anterosuperior iliac spine); (34) Right RASIS; (35) Right PSIS (posterior superior iliac spine); (36) Left PSIS; (37) Left LASIS (left anterosuperior iliac spine); (38) LASIS; (39) ASIS (anterosuperior iliac spine) Midpoint; (40) Sternal Notch; (41) Right Acromion Process; (42) T3; (43) Left Acromion Process; (44) Right Posterior Shoulder; (45) Right Auxilla; (46) Right Anterior Shoulder; (47) Mid Sternum; (48) T4; (49) Right Max Pectoral; (50) Right Max Pectoral Lateral; (51) T6; (52) Left Max Pectoral Lateral; (53) Left Max Pectoral; (54) Left Auxilla; (55) Xiphoid Process; (56) Right Bottom Rib; (57) T8; (58) Left Bottom Rib; (59) Right arm Deltoid Insertion; (60) Right arm Mid Tricep; (61) Right arm Mid Tri-Bicep; (62) Right arm Mid Bicep; (63) Right arm Lateral Humeral Epicondyle; (64) Right arm Olecranon; (65) Right arm Medial Humeral Epicondyle; (66) Right arm Bicep Insertion; (67) Right arm Lateral Maximal Forearm; (68) Right arm Posterior Maximal Forearm; (69) Right arm Medial Maximal Forearm; (70) Right arm Anterior Maximal Forearm; (71) Right arm Radial Styloid; (72) Right arm Mid Extensor Tendons; (73) Right arm Ulnar Styloid; (74) Right arm Mid Flexor Tendons; (75) Right hand 2nd Met-Phalangeal joint; (76) Right hand Posterior 3rd Phalanx; (77) Right hand 5th Phalangeal joint; (78) Right hand Anterior 3rd Phalanx; (79) Left arm Lateral Humeral Epicondyle; (80) Left arm Medial Humeral Epicondyle; (81) Left arm Radial Styloid; (82) Left arm Ulnar Styloid; (83) Left hand 2nd Met-Phalangeal joint; (84) Left hand 5th Phalangeal joint; (85) Top of head; (86) Bridge of Nose; (87) Right Temporal Mandibular; (88) Occipital Tuberosity; (89) Left Temporal Mandibular.

The following indicates the segment locations of landmarks, with those at joints or boundaries between adjacent segments frequently being shared by both segments. The reference numbers refer to those shown in parentheses in the previous paragraph. Right foot 1, 2, 3; Right ankle 4, 5, 6, 7; Right lower leg 8, 9, 10, 11; Right knee 12, 13, 14, 15; Right upper leg 16, 17, 18, 19, 20, 21, 22; Left foot 23; Left ankle 24, 25; Left lower leg None; Left knee 26, 27; Left upper leg 28; Pelvis 29, 30, 31, 32, 33, 34, 35, 36, 37, 38, 39; Middle trunk None; Upper trunk group 40, 41, 42, 43, 44, 45, 46, 47, 48, 49, 50, 51, 52, 53, 54, 55, 56, 57, 58; Right upper arm 59, 60, 61, 62; Right elbow 63, 64, 65, 66; Right lower arm 67, 68, 69, 70; Right wrist 71, 72, 73, 74; Right hand 75, 76, 77, 78; Left upper arm None; Left elbow 79, 80; Left lower arm None; Left wrist 81, 82; Left hand 83, 84; Head 85, 86, 87, 88, 89.

The mid-upper trunk and arm sensors are attached to a special purpose, adjustable, close-fitting jacket, with sewn-in sensor pockets and elasticated Velcro™ straps to retain and position the sensors close against the player's body. The jacket is made from netted material to allow air circulation and increase player comfort. The hand sensors are attached to gloves, again with sewn-in pockets and elasticated Velcro retaining straps. The leg sensors are attached to pockets on elasticated Velcro straps, usually fitted outside light trousers worn by the player. The head sensor is attached to a light hat which closely follows the movement of the head. Wires from the sensors are directed to the rear of the jacket, which supports their weight. From this point, the wires are gathered together and neatly trailed in an unobtrusive suspended umbilical-cord-type arrangement to a central data collection means.

Tests have shown that this method for calculating BSIPs provides very satisfactory levels of accuracy. It is also relatively fast, reliable and convenient, with a single operator typically completing all measurements on a person of average physique in about twelve to fifteen minutes. The system is also convenient and cost effective in that it uses the same apparatus as is used for motion capture of the joints and club.

Figure 6:
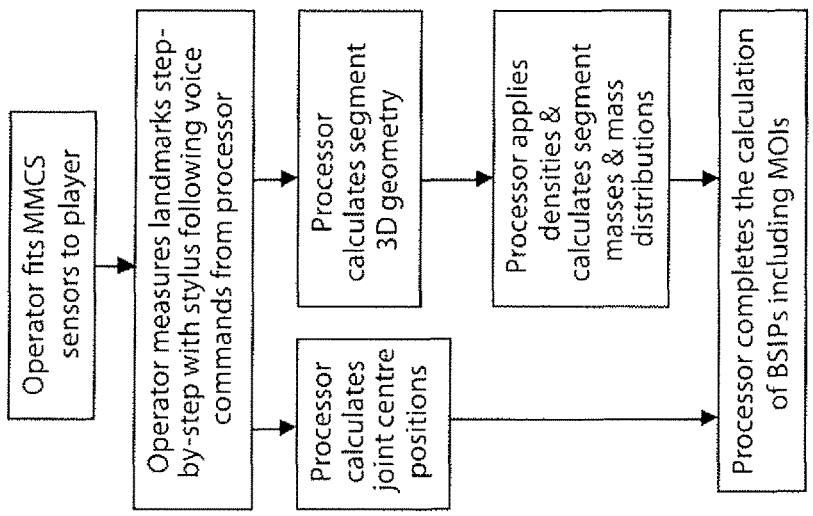

FIG. 6 shows a diagram depicting some of the steps involved in the palpated example for measuring BSIPs with a stylus, as described above. The abbreviations MMCS and MOI signify 'magnetic motion capture system' and 'moment of inertia', respectively.

Where a joint is tracked by a different sensor on each of two adjacent segments, the position of the joint centre can be determined by programming the system to search for the point which is closest to being stationary relative to the two segments sharing the joint, when various defined movements of the joint take place. The optimum position for the joint centre will correspond to this point. For convenience, this technique for finding joint centres will be referred to as the 'common-centre' technique. The defined movements can be chosen to represent the possible degrees of freedom of the particular joint which are most relevant to the golf swing. Accuracy in this determination can be increased by arranging the defined movement to be as large as can be comfortably carried out, within the limits of a golf swing, and of a magnitude which does not cause significant or undue movement of the sensors due to skin movement relative to the joint. Accuracy can also be increased by careful selection of sensor positions. For example, sensors may be positioned on areas of the segment surfaces which are less likely to be disturbed by underlying muscle activation. Accuracy can additionally be increased by positioning sensors such as to increase their radial distance from the joint, proportionately lessening the effect of sensor movement. The technique may be used alone or may be used in conjunction with geometric palpation techniques, as earlier described, to find the joint centre.

In the case of the hip joint, the relevant sensors are those of the pelvis and upper leg. This joint is particularly suited to determination using two sensors, being close to being a true spherical joint acting with three degrees of freedom. The defined movement may include rotary swaying of the hips. In the case of the knee joint, the relevant sensors are those of the upper and lower legs. Because this joint is less accurately represented as a true spherical joint, the method may be used in conjunction with geometric palpation techniques. However, it will provide the best estimate of joint centre in the plane in which its major movement of flexion and hyperflexion occurs.

A variation of the common-centre technique can also be used where a joint is tracked by a sensor on just one of its adjacent segments, which will be referred to as a first segment. In this instance, the player consciously locks, in so far as is physically possible, the joint between the adjacent segment which does not have a sensor and the next segment along the chain, such that the sensor on this next segment tracks the position of the two segments locked together, allowing the joint between this pair of locked segments and the first segment to be subjected to the common-centre technique. Typically, the player executes particular defined movements of the joint being investigated which facilitate the player in keeping the segments adjoining the adjacent joint locked in fixed relationship to each other. This variation reflects a further aspect of the invention and shall be referred to as the 'locked-common-centre' technique elsewhere in the description. Particular examples of the locked-common-centre technique are given where elbow joint positions are found using locked wrist joints, outer shoulder joint positions are found using locked inner shoulder joints, and inner shoulder joint positions are found using locked outer shoulder joints.

The locked-common-centre technique can also be advantageously used to determine joint centres by locking joints which are not present in the jointed segment model. For example, in the present embodiment the model comprises a single neck joint between the head and mid-upper trunk, even though in reality the neck is capable of bending at points along the spine above the model's neck joint. Where the locked-common-centre technique is used to determine the position of the neck joint, the player locks the head and portion of anatomical neck above the joint when executing the defined movements.

It is noted that the common-centre and locked-common-centre techniques can be used in several different ways in the present invention. For example, it may be used to determine joint centres in relation to anatomical landmarks on players in general on a once-off basis, following which joint centres are determined by establishing the relevant landmarks on specific players. Alternatively, it can be directly used to determine the specific joint centres of players on an individual basis.

Use of Surface Measurement and Depth Cameras to Measure BSIPs

Although stylus palpation and geometric modelling of the types described will typically be much more convenient and give much greater levels of accuracy than prior art methods of determining BSIPs, a further aspect of the invention relates to an insight that even greater levels of accuracy can be achieved using a system which scans or measures the surfaces of a player's body in a practical manner.

A first example of a method for achieving this involves use of one of the sensors of the magnetic motion capture system, such as the stylus sensor, to develop segment surfaces within the system software, and subsequently calculate segment volumes and volume distribution from these surfaces. The surface is developed by the operator quickly running the stylus over a limited number of relevant representative portions of the segment surface and holding down its operating button, causing a succession of surface points to be measured and recorded. The process may be automatically ended by the processor when sufficient points have been recorded to allow accurate estimation of the total segment surface. The operator avoids portions of the surface obstructed by the sensors and other bulky apparel. It remains necessary for the operator to measure anatomical landmarks associated with joint positions, as previously described.

The surfaces of the player's body can also be measured in a practical manner with a 3D or depth camera system, which has the added advantages of requiring less operator skill and avoiding direct apparatus contact with the player. Tests have indicated that 3D camera systems can reduce typical errors in determining segment moments of inertia, arising from inaccuracies in determining segment shape and volume distribution, to about half or one third of those which occur when measuring using stylus palpation and geometric modelling, as previously described.

3D camera systems use various known methods to obtain 3D depth information, including structured light, time-of-flight and stereo imaging. Their ability to determine 3D depth also makes them proficient at separating the subject from the background. The 3D camera may comprise inbuilt software capable of image processing, extraction of a jointed segment model of a human subject and motion tracking of the jointed segment model. Systems with inbuilt software of this type, which will henceforth be referred to as 'enhanced 3D cameras', are widely used in computer based gaming, and are compact and relatively inexpensive. Standard jointed segment models of human subjects typically include about twenty joints. In the examples which follow, the term enhanced 3D camera shall also be understood to refer to a combination of a 3D camera operating with any software which extracts or tracks a jointed model, including software operating on a processor which is not an inherent part of the 3D camera system.

Measurement of BSIPs using a practical scanning device, such as a 3D camera, has several potential relative advantages over the previously described stylus palpation method. The most important of these is the potential for greater accuracy and consistency. Other advantages include the potential to take far less time and thereby increase user convenience and reduce testing costs and the potential to use less skilled operators. A further advantage relates to the potential to avoid physical contact between player and operator. Measurement of BSIPs using devices such as 3D cameras, also has potential disadvantages. These include cost and complexity of additional apparatus, cost and time involved in developing and integrating the 3D camera system, and inconvenience or unpleasantness for the player of being required to wear minimal clothing during part of the process.

In a second example of a practical system which measures the surface of a player's body, a 3D camera (3DC) is used to measure parameters relevant to segment shapes and a magnetic motion capture system (MMCS) and palpation technique are used to measure parameters relevant to joint centres, the two systems being used at different times or stages which may be in different locations. In a variation of this example, the 3DC is an enhanced 3DC. Other types of motion capture system and joint determination procedures may also be used.

In the stage where parameters are measured relevant to segment shapes, the player stands in the field of the 3DC wearing minimal clothing and executes relevant poses or motions. The 3DC, or combination of 3DC and system processor, measures visible portions of the surfaces of the player's segments.

In the stage where parameters are measured relevant to joint centres, the player stands in the field of the MMCS with multiple segment sensors fitted. An operator palpates the player with a sensor stylus and the system determines the joint centres, generally as described earlier in this description. The system processor constructs a basis for the model of the player from the joint centre positions in a format relevant to inverse dynamics calculation, this model including segment reference frames. References to operations carried out by the processor throughout the description include operations carried out by conventionally prepared software operating on the processor.

The processor obtains the information relevant to segment shapes and fits the constructed shape to the player partial model. This may be done in various ways. For example, segment ends, with respect to their position in the jointed chain of segments, may be determined from constructed segment shapes, and the joint centres of the constructed segment shape assumed to positioned at segment ends. This allows the constructed segment shape to be matched to the joint centres of the partial model. Alternatively, segment shapes may be matched to potential segment shape ranges or templates constructed within the partial model. In a further alternative example, joint centres my be determined for the segment shape using the joint determining capabilities of an enhanced 3D camera, which comprises inbuilt software capable of image processing, extraction of a jointed segment model of a human subject and motion tracking of the jointed segment model. The joint centres of the segment shape are then matched to the joint centres of the partial model. In yet a further alternative example, joint centres are determined for determined segment shapes using the common-centre or locked-common-centre techniques, described elsewhere, and matched to the joint centres of the partial model. In the common-centre technique, the position is determined as the point which is closest to being stationary relative to two adjacent segments when movement of the joint takes place. In the locked-common-centre technique, the position is determined as the point which is closest to being stationary relative to a first segment and combination of two segments when movement of the joint takes place when the player consciously locks the joint between the combination of two segments, where the position is common to an adjacent first segment and an adjacent combination of two segments.

When each segment shape is fitted to the relevant segment reference frame or set of joint centres of the partial model, the processor applies relevant densities to the segments and calculates the player's BSIPs, including relevant moments of inertia. These density values may be the same or similar to those given earlier in this description.

It is usually more convenient to group certain combinations of segments where segment shapes are determined by optical depth determination. In particular, the somewhat arbitrary segments of the trunk, including pelvis, middle trunk, mid upper trunk and left and right upper trunk segments may be measured and determined as a single combined segment, because the complicated shape is relatively easily measured and determined by optical depth determination, in contrast to the notional boundaries between the component segments which are arbitrary and relatively difficult to measure or determine. Separate measurements and determinations may be made of the combined trunk segment in an upright symmetrical position and in a leaning-forward or ball address position. The combined trunk segment can be relatively easily fitted to the partial model when the outer shoulder and hip joints of the partial model are known.

Although these calculated BSIPs may be used in other swing tests, it will usually remain necessary to repeat the determination of joint centres each time swing tests are carried out with the MMCS, unless means are found to ensure that sensors of identical characteristics can be positioned in identical positions on the player's body. For so long as the player does not significantly change overall body mass and mass distribution across segments, the BSIP details may be repeatedly used over swing tests. Checks for changes in BSIP details may be readily made by checking if the player has changed overall body mass using a conventional weighing scales.

Accuracy may also be improved at each primary measurement of BSIPs by appropriately adjusting BSIPs of all segments based on a comparison of the player's overall mass with the sum of the calculated masses of all the player's segments. The player's mass is readily determined with an accurate weighing scales and adjustment made within the calculation software relative to the calculated segment masses. These improvements can be implemented with minimal inconvenience to players.

In the first stage, measurement takes place with the player in view of the 3D or enhanced 3D camera. The motion capture system is not used and sensors are not positioned on the player. The player wears minimal clothing and that which is worn is close fitting. Where necessary, the player wears a close fitting cap or net to hold hair close to the head. The player wears the same or similar shoes to those which will be used in swing testing. To afford privacy and comfort to the player, this first stage may take place in a separate secluded space. On instruction, the player executes a series of poses and motions which are selected to reveal the shapes of segments and the positions of joints. In particular, they include poses and motions which expose the articulation of segment joints to clear enhanced 3D camera views, including poses with legs well separated and arms outstretched. They also include poses with joints across their normal ranges of displacement, including positions as close to the extremes as is practicable, convenient and comfortable for the player. The poses and motions include ones displaying front, rear and side views. They also include poses and motions relevant to the upright position of the player, such as that which corresponds to the top of backswing, and the leaning forward position of the player, such as that which corresponds to the position coming up to impact. Instruction may be given by an operator, may be given automatically by the system or may be read from a display screen or instruction document by the player.

An important advantage of the method in this example results from the separation of the 3DC and MMCS stages, only requiring the player to wear minimal clothing during the 3DC process, which can be carried out away from the main test area with relative privacy, and allowing the player wear more normal clothing during actual swing testing. Minimising clothing in the 3DC stage increases the potential accuracy of segment shape measurement.

FIG. 7 shows a diagram depicting some of the principal steps involved in the system for measuring BSIPs using a 3D camera or enhanced 3D camera, as described above. In this example, constructed segment shapes are fitted to segment reference frames. The abbreviations 3DC, MMCS and BSIP signify '3D camera', 'magnetic motion capture system' and 'body segment inertial parameters', respectively.

In a third example of a practical system which measures the surface of a player's body, a 3D camera (3DC) is again used to measure parameters relevant to segment shapes in a manner similar to that described in the second example. However, in this instance, parameters relevant to joint centres are measured without recourse to palpation techniques and involve the use of a 3DC and MMCS. This provides the additional advantages of decreasing the amount of time required to measure the player and reducing the necessary level of skill required by the operator. It also increases the consistency of results by reducing the influence of individual operator skills.

The player stands in the field of the MMCS with multiple segment sensors fitted and executes a routine of poses and motions. The processor determines parameters relevant to the locations of joint centres, relative to the positions of the segment sensors, from these poses and motions. The processor uses these parameters, together with other information available to it, to determine improved estimates of joint centres. When determining joint centres, the processor uses various particular techniques related to those described elsewhere in this document. For example, where a joints lies between two segments with sensors attached, the joint centre is found by techniques equivalent to the common-centre technique, essentially determined as the point which displays least movement relative to the two sensors.

Other information available to the processor in determining joint centres includes position symmetry information, known relationship between joint centre information, and position information related to known average human geometry. Position symmetry information assumes left and right ankle, knee, hip, inner shoulder, outer shoulder, elbow, and wrist joints are symmetrical about a vertical sagittal plane bisecting the player when the player stands in a balanced upright position. It also assumes that lumbar, thorax and neck joints lie on this sagittal plane. Position symmetry assumes equal distances between joint centres on left and right lower legs, upper legs, upper arms and lower arms. It also assumes equal distances between joint centres between left and right hips to lumbar, thorax to inner shoulder and inner shoulder to outer shoulder. Known relationship between joint centres information includes, for example, the assumption that the distance between left and right hip joints remains substantially constant for all positions of the human body. Individual hip positions determined by other methods may be altered and improved by determining the positions which best satisfy constant distance between hips across the range of movements. Position information related to average human geometry is largely used to fill gaps where information is more difficult to measure, such as the geometry of the inner and outer shoulder joints. The average values are appropriately scaled to the player model, for example by scaling to lengths between joints which can be determined with a high degree of accuracy, such as those determined by techniques equivalent to the common-centre technique or locked-common-centre techniques.

Other information available to the processor in determining joint centres may also include estimates of joint centres obtained from the 3DC where this is an enhanced 3DC. Where such estimates are used, the poses and motions executed by the player in the field of the 3DC are additionally selected to reveal the positions of the joints. These include poses and motions with joints across their normal ranges of displacement, including positions as close to the extremes as is practicable, convenient and comfortable for the player. They also include poses and motions which expose the articulation of segment joints to clear 3D camera views, including poses with legs well separated and arms outstretched.

An algorithm, or set of algorithms, within the processor software, takes all such available information into account, when determining the overall joint centre model. Appropriate weightings are applied to items of information relative to their expected levels of accuracy. For example, knee, and hip joint centres determined by the 3DC are likely to have lower weightings that knee and hip joint centres determined by the MMCS. Similar to the first example, the processor effectively uses these various data obtained from the 3DC and MMCS to construct a model of the player with individual segment reference frames fitted with the determined segment shapes. The processor similarly applies relevant densities to the segments and calculates the player's BSIPs, including relevant moments of inertia.

FIG. 8 shows a diagram depicting some of the steps involved in this third example of a system for measuring BSIPs where means are used to measure surfaces of the player's body. The figure uses similar abbreviations to those used in FIG. 6.

In a fourth example of a practical system which measures the surface of a player's body, a 3D camera and MMCS are again used to measure parameters relevant to segments shapes and joint centres, similar to that described in the third example, but in this instance the fields of the 3D camera and the MMCS occupy a common location and measurements may be taken simultaneously. This provides the potential advantage of not requiring a separate 3D camera stage, which may reduce measurement time and cost for the player and operator.

The player simultaneously stands in the field of the 3D camera and in the field of the MMCS with multiple segment sensors fitted and executes a routine of poses and motions. The processor aligns the reference frames of the 3D camera and the MMCS. The 3D camera determines segment shapes, in a similar manner to that described in the second and third examples. The processor uses all available information, including information from the MMCS, to determine joint centres, in a manner similar to that described for the third example.

Similar to the second and third examples, the processor uses these various data obtained from the 3DC and MMCS to construct a model of the player with determined joint centres and with individual segment reference frames fitted with the determined segment shapes. The processor applies relevant densities to the segments and calculates the player's BSIPs, including relevant moments of inertia.

A compromise is made between wearing clothing which is convenient and comfortable for the player, and minimising distortion of player outlines and surface depths, by wearing close-fitting and minimal clothing. An open body harness may be used to support the MMCS sensors instead of a jacket. The system software is arranged to allow for or disregard sensors, sensor supports and sensor wiring. This may, for example, involve colouring these components such that they are recognised and appropriately handled by the system software. The system software comprises an algorithm which estimates an allowance for clothing thickness, based on predetermined adjustment factors.

Figure 9:
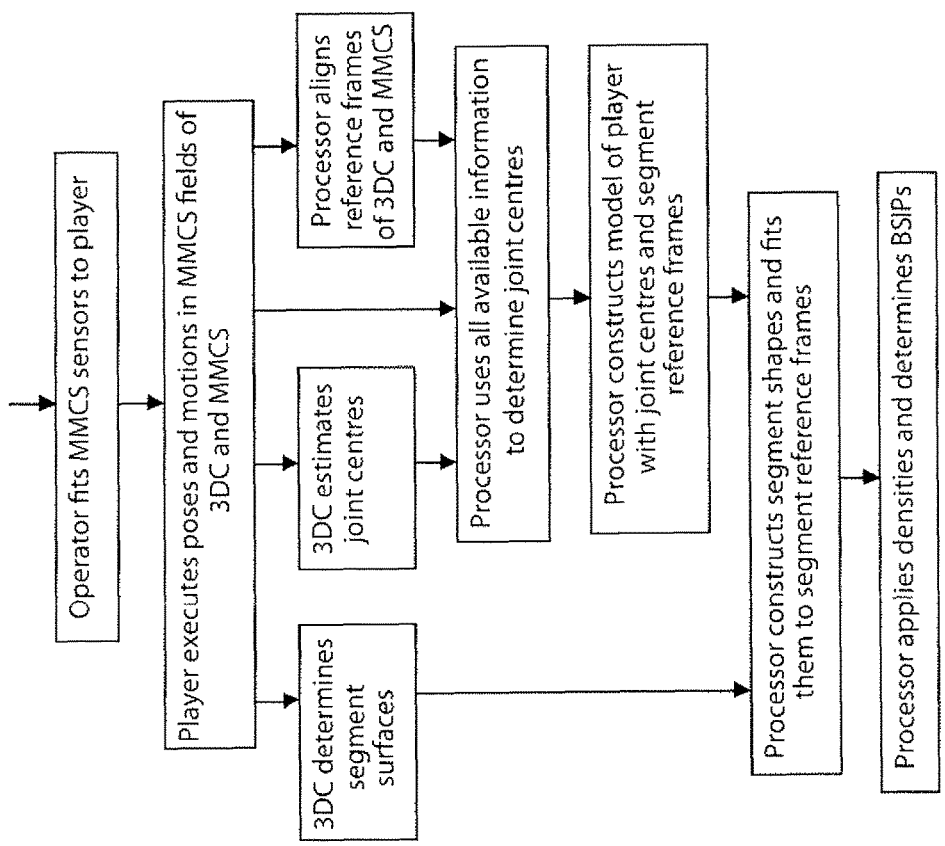

FIG. 9 shows a diagram depicting some of the steps involved in this fourth example for measuring BSIPs where means are used to measure the surfaces of a player's segments. The figure uses similar abbreviations to those used in FIG. 6.

In a fifth example of a practical system which measures the surfaces of a player's body, a 3D camera is used in conjunction with a magnetic motion capture system, with the 3D camera attached in fixed relationship to a sensor which is tracked within the magnetic field of the motion capture system. This may be arranged, for example, by attaching the system stylus sensor to the 3D camera. The 3D camera and attached sensor are used to measure the shapes of the player's segments.

Similar to the first example, this method has the potential advantage of allowing an operator scan the player with a hand held device rather than having to rely on the player executing particular poses and motions required for obtaining segment shapes. Because the camera and attached sensor are tracked in the same magnetic field as the player's body segment sensors, it doesn't matter if the player moves when being scanned. Body scanning of this type can typically be executed in less than one or two minutes.

Joint centre positions, relative to the magnetic field of the MMCS, may be measured by any suitable method, including those set out in any one of the previous examples or described earlier using stylus palpation methods. Joint centre positions may also be determined using the 3DC attached to the sensor, or by a combination of this method with another method.

Similar to the previous three examples, the processor effectively uses these various data obtained from the 3D camera and MMCS to construct a model of the player with determined joint centres and with individual segment reference frames fitted with the determined segment shapes. The processor again applies relevant densities to the segments and calculates the player's BSIPs, including relevant moments of inertia.

Figure 10:
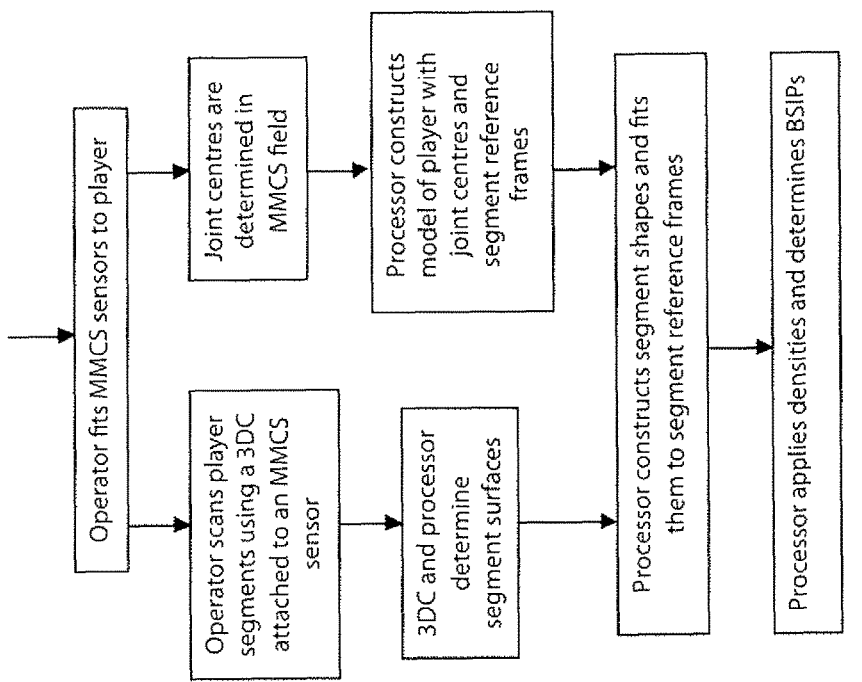

FIG. 10 shows a diagram depicting some of the steps involved in this fifth example of a system for measuring BSIPs using means to measure the surfaces of a player's segments. The figure uses similar abbreviations to those used in FIG. 6.

Combinations of elements from the five examples described above may also be advantageously used, depending on particular requirements of the system. The methods described in the examples may also be applied to other types of motion capture system used as the primary means for obtaining kinematic information on the swing, including high speed camera systems.

Further Details of Apparatus and Methods

A further difficulty in successfully applying inverse dynamics calculations or similar techniques lies in correctly identifying, throughout the downswing or swing, the points of application of GRFs in relation to the movement and BSIPs of the player. This identification is of great importance because even small errors in the identification can cause significant effects in the accuracy of the calculations. The problem is overcome in the present examples by using the stylus to additionally reference the positions of the force plates relative to the reference frame of the system, thus using a highly accurate and unified reference system for all of these relevant measurements. Where the force plates comprise metals which would interfere with the operation of the stylus, a moveable, non-metallic, rigid calibration fixture is placed in accurate registration on top of the force plates. The calibration fixture comprises landmark points which are at a sufficient distance above the force plate surfaces to allow the stylus to identify them without interference from force plate metals. The fixture is removed when readings referencing the force plates are taken.

Another potential difficulty with the measurement system relates to the impracticality of mounting an active sensor, of the typically available type, on or close to the clubhead. This impracticality arises for the following reasons. It is likely to interfere with the natural movement of the clubhead, it is likely to be damaged or dislodged at impact, and sensor operation is likely to face interference from metal in the clubhead. These prevent use of a clubhead sensor for detecting the time instants of takeaway and impact. The difficulty is overcome in the present arrangement by the following means. The position of the contact face of the clubhead is registered in relation to the sensor mounted on the club shaft using the stylus in the manner already described. This allows the position of the clubface to be monitored where the relative position of the clubface and club shaft remain unchanged, as is the case at takeaway. The time of takeaway is thus determined as the time when the clubface moves away from the region of the ball and continues into the backswing movement. This method cannot, however, be used to determine the time of impact both because significant relative movement will take place between the club shaft and clubhead from forces acting during the high speed downswing and because the scanning speed of the motion capture system is insufficiently fast to accurately capture the high speed clubhead at impact. The time of impact is instead determined by using one or two strategically positioned microphones which separately detect the sound of the club striking the ball. Microphone detection is synchronised with the kinematic measurements and allowance is made for the speed of sound. Where two microphones are used, the time difference between detection at the first and second microphones is used to screen out detected sounds which do not originate at the region of impact. An alternative method involves use of the system sensors or force plates to detect the impact event, making allowance for the brief delay which occurs as the shock wave travels along the club and through the player's body to the force plate sensors. The sensor on the club shaft cannot be used alone to accurately obtain this information because its scan rate is too low, although it can be used to indicate a time range where the shock wave can be detected on the force plate recorded data. The force plate scanning speed can be increased to improve detection accuracy. Force plate scanning speeds can usually be increased without penalty because they typically produce an analogue signal detected by wire.

In prior art, signals from the sensors of the motion capture system and force plates are usually smoothed to reduce random signal noise. Typically, smoothing is carried out with a digital filter. Although commonly used, simple digital filters, such as moving average filters, tend to obliterate some of the relevant features of the signal. More refined digital filters, such as Butterworth low pass filters, are frequently used in higher level applications, because they are better able to preserve signal characteristics. An aspect of the invention involves an appreciation that even the best of these prior art digital filters do not perform well when filtering signals used for calculation techniques such as those used in inverse dynamics in high acceleration actions like the golf swing, and in particular movements involving abrupt changes in velocity, such as occur at the impact event. Although filters of the Butterworth type can isolate the frequency content of a signal, they cannot distinguish when these components occur in time. They also tend to widen and attenuate higher frequency transients of the signal, including those produced by impact. They can cause further problems when presented with automatic filtering of a range of signals, such as input signals from sensors tracking different body segments, since these will tend to have different optimal frequency requirements. This is due to such filters usually being limited by the selection of optimal cut-off frequencies, as the signals from different sensors will usually have different optimum cut-off values and the same low pass filter is typically used for all motion capture or all force plate sensors. Filtering is of particular importance in inverse dynamics calculations because of the dependence on accelerations obtained from noisy positional data. Acceleration is obtained by double differentiating the positional data with respect to time, which magnifies random errors or noise in the signal and introduces significant errors into the calculations. Furthermore, such errors tend to accumulate as inverse dynamics calculations proceed through the chain of segments. Another problem area relates to the impact event. Sudden large changes in velocity and acceleration around this event can prevent meaningful differentiation of the positional signal to obtain time derivatives, because the data collection speed is slow relative to the speed of the club near impact. Too many time derivative data points are lost prior to impact to satisfactorily resolve the problem by extrapolation where pre-impact data alone is considered. Where pre-impact and post-impact data are included in the data presented to a smoothing filter, it will usually not be able to distinguish between true acceleration produced by the impact and spurious accelerations produced by noise in the data, typically resulting in over smoothing of the data.

These problems in prior art are overcome by various techniques. One such technique is to develop and use filters which have the ability to localise the frequency content of the signal. This can be potentially achieved by filters which transform the noisy data into the frequency domain by means of a transformation, such as a wavelet or Fourier transform. Another such technique is to provide each sensor associated with measurement of a particular body segment or particular force plate output, with a filter which is appropriately and individually modified to provide optimum performance. Yet another such technique is to reduce problems associated with differentiation of data by filtering or removing noise from the parameter which precedes the final differentiation. Thus acceleration is obtained from filtered velocity data which has been obtained from the original unfiltered positional data, in contrast to the conventional method, where acceleration is obtained by double differentiating filtered positional data.

Figures 11, 12:
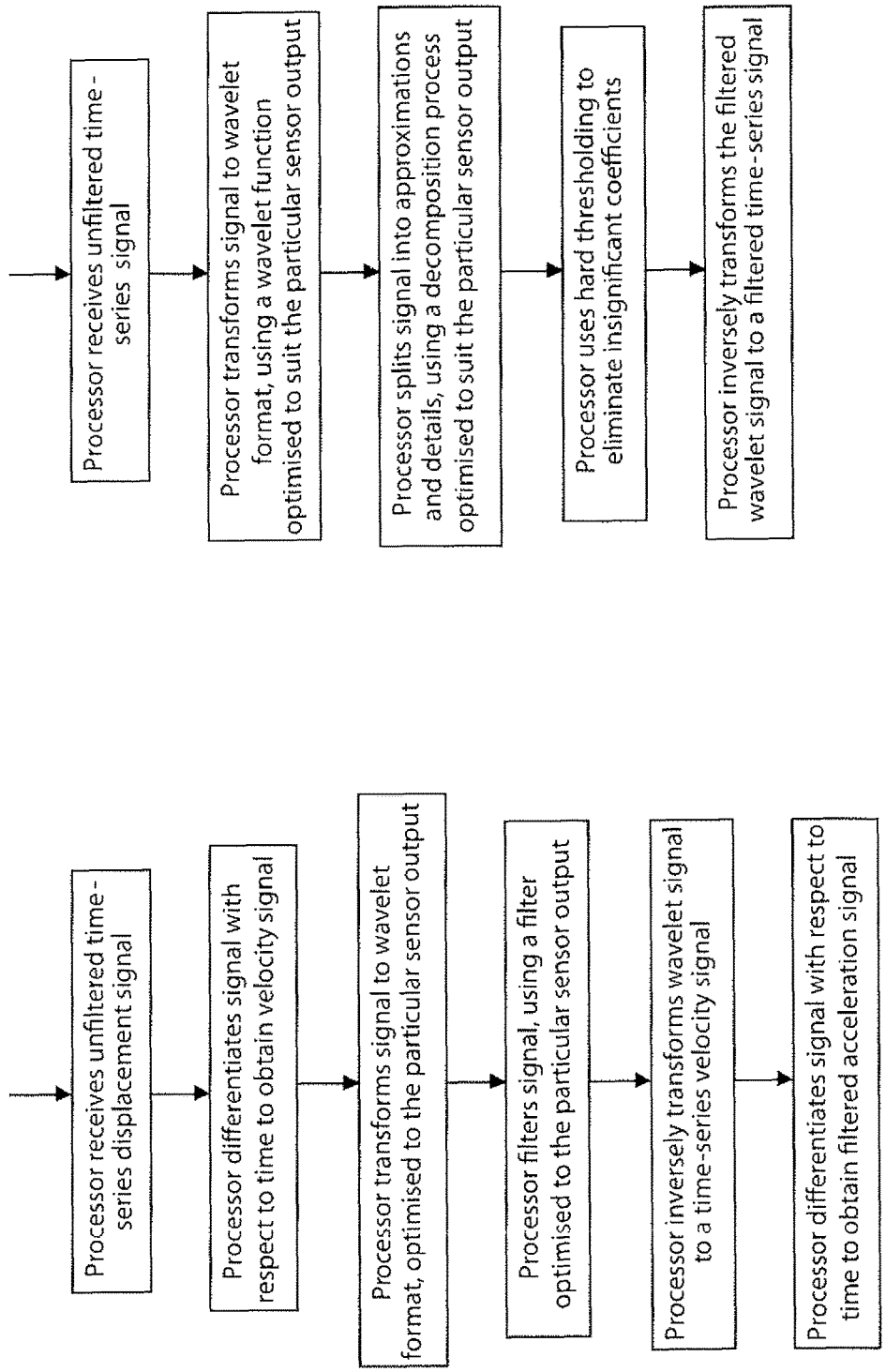

These techniques are illustrated in FIG. 11 which shows a simplified block diagram depicting steps involved where an unfiltered displacement signal is converted to a filtered acceleration signal.

In the present example, wavelets are used to filter the signals. The shape of the signal is decomposed into different wavelets, thresholded to remove noise, and then reconverted to a filtered time-series signal. The system is suitable for automatic operation with a variety of signals from sensors with varying signal frequencies, as occurs with the apparatus of the present invention.

It is important to select the optimum wavelet function, or mother wavelet, to fit the specific application to obtain the best characterisation of the frequency content of the signal. This is done by trialling different wavelets and using cross correlation or auto correlation methods to find the one which maximises the correlation coefficient. The method produces a coefficient whose magnitude is related to how well the mother wavelet fits the data, i.e. how similar it is to the signal. Tests have shown that sensors measuring different segment movements usually have different optimum mother wavelets.

The wavelet representation of the signal is decomposed by splitting it into approximations and details. The approximations are the high-scale, low-frequency components of the signal and the details are the low-scale, high-frequency components. The original signal is passed through two complementary filters and emerges as two signals, the approximation and the detail. The decomposition process is iterated, with successive approximations being decomposed in turn, so that the signal is broken down into many low resolution components. It is important to optimise this decomposition process. During the wavelet filtering process the signal is first cropped or padded to a dyadic length, that it is some power of two. The decomposition stage decomposes the signal into a maximum of J−1 scales, where J is the power, so for a signal of dyadic length 1024, the maximum number of scales the signal can be decomposed into is J−1=10−1=9. The wavelet filtering process chosen always decomposes the signal into the maximum number of scales so that thresholding can be applied to every level.

The decomposed signal is then subjected to a hard thresholding technique where noise is removed by eliminating coefficients that are insignificant to thresholds set to a multiple of the standard deviation of the amplitudes of the wavelet coefficients at each decomposition level. This is achieved using empirical observation and judgement across a large number of signals to select the optimum values.

Translation invariant removal of noise has also been found to be useful in suppressing artefacts that can appear near singularities in the data by averaging out the translation dependence. Finally, the filtered wavelet signal is inversely transformed back to a time-series signal. When mother wavelet selection and decomposition and threshold processes are optimised for each particular sensor types, these optimised parameters are used in all further applications.

To obtain filtered acceleration and velocity outputs from raw positional signal, filtering is carried out on the variable which precedes the final differentiation. In practice therefore, where acceleration is required, velocity rather than displacement is filtered. This solution was established by trial testing of signals from magnetic motion capture of golf swings, where all combinations of filtering of displacement and velocity were tested. Filtering solely of velocity signals was found to give optimum results. It is not known if this result applies to signals from other types of motion capture system.

FIG. 12 shows a diagram depicting some of the steps involved where these techniques are used to filter a signal.

As mentioned earlier, a further problem relates to the abrupt change which occurs when the clubhead impacts the ball, with the clubhead sharply decelerated over a time period which is much shorter than the scanning period of the motion capture system, causing a discontinuity in the acceleration data through the impact event. Even when the improved filtering system mentioned above is used, this prevents accurate double differentiation with respect to time being carried out for several scans periods just before and just after impact. For example, a loss of four scan periods before impact at a scan rate of 240 Hz and a clubhead speed of 50 m/s will give rise to absent data over about 4.2 ms, during which time the clubhead would have travelled over 200 mm if it continued at this speed. A similar, although smaller, loss of data would occur after impact. Where proper account of this step change is not made and data is filtered or smoothed through impact, significant distortion of data around impact will occur, even where noise error has been satisfactorily removed from the positional data. This problem in determining the changing clubhead, or velocity profile, is overcome in the present invention in the following way. Ball velocity is measured after impact and is used to determine the step change in clubhead velocity, since the combined momentum of the clubhead and ball remains constant and the mass of the clubhead and ball are either known or readily determined. This step change may, for example, be assumed to occur at a steady rate of acceleration over the typical time duration of impact, which is known to be about 0.45 ms. Knowledge of this step change is then used to adjust clubhead speed approaching impact, through impact and after impact, provide an improved construction of clubhead velocity through the impact event, and is used to link together and shape the best estimated measure of velocity up to impact from the pre-impact data and the best estimated measure of velocity immediately after impact using the post-impact data. Ideally, clubhead velocity curves are filtered and calculated up to impact, and calculated from post impact back to impact, and then adjusted to allow for the calculated step change in clubhead velocity at impact. The information required for this calculation will frequently impose little or no burden on the system, because clubhead mass must in any event be known for the general inverse dynamics calculations, ball mass varies very little, and most testing will measure ball velocity as a general evaluation of the swing.

Figures 13, 14:
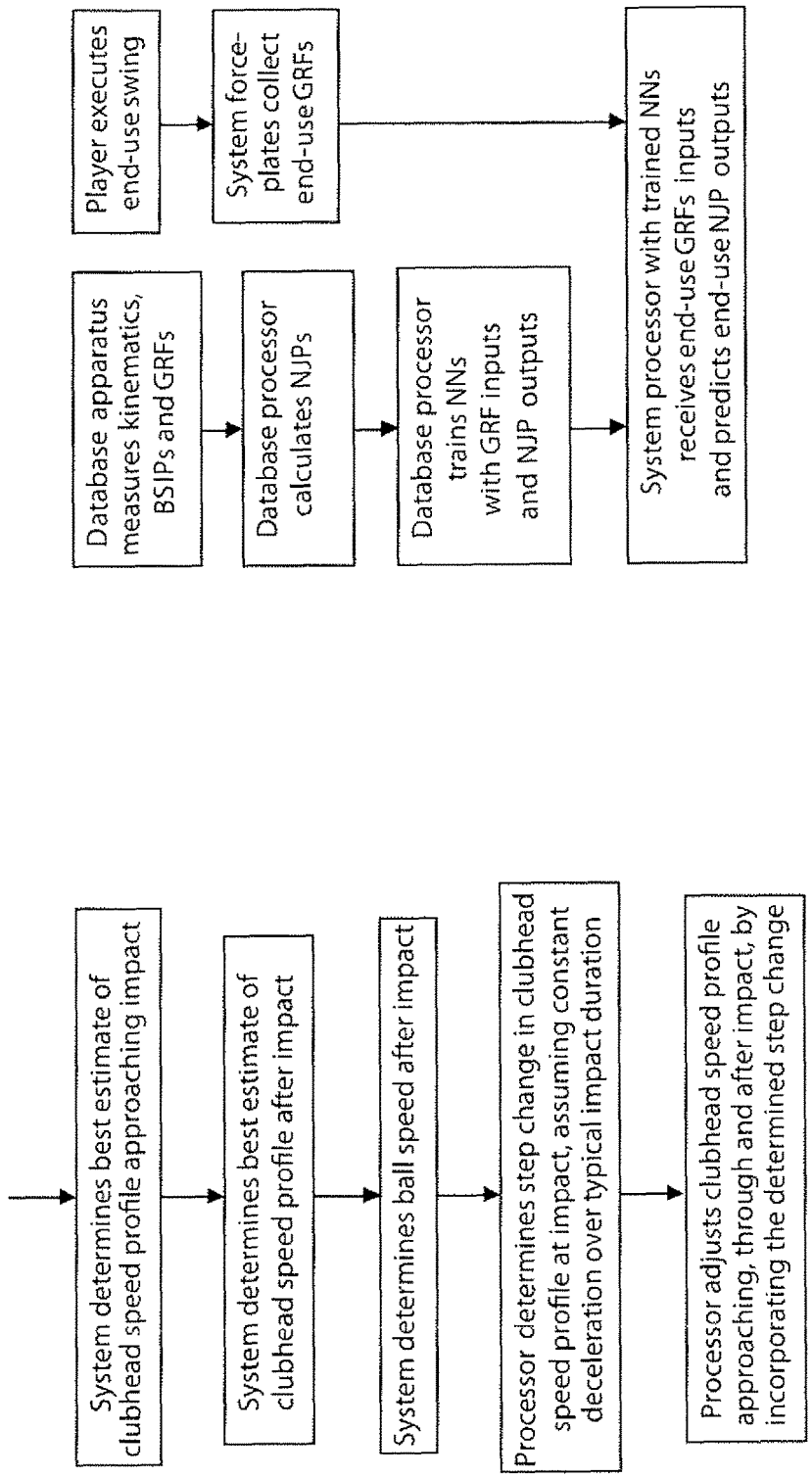

FIG. 13 shows a diagram depicting some of the steps involved where these techniques are used to improve the determination of clubhead velocity profile through the impact event.

Quality Assurance

When complex kinematics and GRFs are measured under time constraints, or where large numbers of tests must be processed, set-up errors may go undetected causing spoiled tests with cost implications, and inconvenience and annoyance to players. These problems are minimised in the present examples by various monitoring checks or techniques, including those set out below.

An initial monitoring check or technique involves an arrangement whereby the system software gradually constructs a model of the player and club on a screen which is immediately visible to the operator, as the anthropometric landmarks or surface contours are measured and recorded. This visible model replicates player movements causing errors, such as measurement of incorrect landmarks or inadvertent movement of sensors, to generate obvious distortions in the visible model. This alerts the operator to any such errors and allows early correction of the fault.

The model may also be advantageously subjected to automated checks by the system processor. Various checks can be automatically carried out when the player's BSIPs are measured but before swing testing commences. One such check compares the symmetry in calculated lengths between joints, between left and right segments of each of the following pairs—lower legs; upper legs; upper arms; and lower arms. Another such check compares the alignment of points related to the player's spine, including the midpoint of a line between the outer shoulder-rotation joints; the thorax joint; the lumbar joint; and the midpoint of a line between the hip joints. This spine-related check may, for example, be made by measuring the deviations of these points from a first order polynomial curve. A further check compares differences in weight determined by weighing-scales and weight determined from BSIP measurement and calculation, making due allowance for the weight of clothing and shoes.

Additional checks can be automatically carried out while swing testing is in progress. One such check monitors calculated joint centres where these can be determined by tracking the joint with more than one sensor, as previously described. This check is most usefully applied to the hip and knee joints. Another such check monitors the alignment of points related to the player's spine, including the midpoint of a line between the outer shoulder-rotation joints; the thorax joint; the lumbar joint; and the midpoint of a line between the hip joints. Similar to the previously described initial spine-related check, it may, for example, be made by measuring the deviations of these points from a first order polynomial curve.

There are several advantageous automatic checks which cannot be carried out until at least one swing test is completed and a set of inverse dynamics calculations carried out. An important check of this type is a comparison of the proximal-to-distal and distal-to-proximal calculations of torque and power at joints where meaningful calculations are carried out from both directions, such as the thorax and lumbar joints. Where a mismatch in the values occurs, this can provide a warning of an apparatus error, such as a faulty or incorrectly wired sensor, or an error made in measurement of body anatomical landmarks or segment surfaces. Another such check involves a comparison between the rate of change of total segment energy and the rate of change of total combined joint power through the swing. In this check, the club is treated as a segment and energy includes kinetic and potential energy.

The processor may respond in different ways to the results of these automatic checks. For example, each check may be associated with two settable threshold levels. A first threshold may trigger an alert warning to the system operator, prompting a check on the system. A second threshold may trigger a more serious warning, preventing continuation of testing until the issues are resolved. The system maintains a record or log of all such warnings, which is useful as an overall check on the system and its operation.

General Inventive Aspects and Advantages

The various aspects of the invention discussed over previous paragraphs, relate to an overall inventive insight that energy generation and transfer in a golf swing can be accurately, practically and usefully measured and analysed using calculation techniques such as inverse dynamics, despite complete failure to do so in prior art where there was clear potential for very significant commercial advantage in meaningful scientifically based analysis.

Numerous obstacles, which have confounded advances in prior art, are simultaneously overcome by the present invention to achieve a successful result. These include proper focus on energy generation at joints and energy transfer across joints along the linked segment chains, together with focus on the downswing portion of the swing. They also include recognising and dealing with problems related to the unusually high accelerations which occur in the golf downswing, and calculating BSIPs with much greater accuracy that traditionally required for human motions which do not have high acceleration elements. They include development of a new jointed segment model with significantly improved joints at the lumbar, thorax, inner shoulder, outer shoulder and grip positions, and middle trunk segment with a mobile centre of mass. They further include accurately measuring parameters related to indeterminacies arising from ground reaction forces and the closed loop of the arms. They additionally include development of improved methods of determining essential acceleration data, including development of improved filtering systems and systems for measuring and processing data around the impact event.

Overcoming these obstacles has resulted in highly accurate systems which produce a meaningful analysis which is of real practical use and therefore has the potential to be of very significant commercial value. They can complete the analysis without human adjustment or manipulation of parameters, and include systems which are fully operational without the need for highly skilled personnel. Resulting systems can also operate in an automatic or largely automatic manner. Some system variations are also suitable for ready transfer and set-up at different sites.

Resulting systems are also suitable for use without assistance from kinematic or kinetic data obtained from previous measurements or analysis. Measurement is carried out in a fast and efficient manner convenient to the player. Measurement and analysis is also carried out at low unit cost. It is carried out with little involvement required from operators, including experts and technicians.

Furthermore, resulting systems are suitable for researching and isolating elements of good and bad play, which can be used in developing and executing golf coaching and training systems, including those ranging from professional to high handicap skill levels. They are also suitable for determining or calculating kinematic and kinetic parameters, including energy generation and energy transfer parameters, with sufficient accuracy to be usable for practical and meaningful individual golf coaching, and with results which can be usefully and meaningfully compared and evaluated against different recorded swings by the same player. Resulting system are also suitable for determining or calculating parameters with sufficient accuracy for use in driving computer models of the golf swing which are usable for practical and meaningful golf coaching or activities related to meaningful golf coaching.

Resulting systems are also suitable for determining or calculating energy generation in a player's body and energy transfer through a player's body and club with sufficient accuracy for use in large scale databases of golf swing information which are usable for practical and meaningful golf coaching or activities related to meaningful golf coaching. Such databases include those suitable for use in training neural networks to predict swing parameters.

In general, swing parameters are measured and determined utilising the model of the player's body in calculations and calculating analysis parameters which are used in analysis of the swing utilising the model and the measured and determined swing parameters. The analysis parameters may provide immediate analysis of the swing or a plurality of analysis parameters may be used to analyse the swing. For example, kinematic and ground reaction force measurements may comprise the measured swing parameters and a calculated analysis parameter might comprise energy generated in a particular joint of the player's body. This particular data may provide immediate information for analysis, or may for example be used by the system processor along with a plurality of other items of determined information on the swing, to give a more general analysis of the swing or on specific aspects of the swing.

Alternative Embodiment of the Invention, Using Artificial Intelligence

In an alternative embodiment of the invention, NJPs are determined by systems and apparatus using a large and representative database of golf swings compiled using techniques for determining NJPs described elsewhere in this description. This database includes GRF data and is used to train an artificial intelligence system, such as a neural network system, to predict or determine the NJPs of new swings, which may be referred to as 'end-use' swings, from analysis of their GRF parameters. GRF parameters include GRFs and moments related to each foot and the combination of both feet, and centres of pressure related to each foot and the combination of both feet. Prediction of swing parameters from GRFs is known in prior art, being disclosed in document WO 2009/060011.

An artificial intelligence system, comprising a set of neural networks, is trained with training inputs including GRF parameters and training outputs including NJPs, both obtained from data recorded for individual swings over the period when the database was prepared. The training NJPs are calculated from measurements or determinations of GRFs, BSIPs and kinematic parameters during the earlier data collection period. The resulting trained networks predict outputs, including NJPs, for new test swings where the inputs include the recorded new test swing GRF parameters. Ideally, separate networks are prepared and used for each numbered iron and wood club type. However, in practice the user will frequently not require all types, and networks for the more commonly used types, or representative types will suffice. Networks may also be trained to accommodate several club types where there is a smooth transformation between types. For example, a network appropriately trained with 5-iron and 7-iron swings will correctly adjust its predictions if an intermediate 6-iron is tested, and to a lesser degree if a 4-iron or 8-iron is tested, because training with 5-iron and 7-iron will have provided it with an ability to scale its results to those differences which occur with club number differences. Although not essential, additional training and test inputs may be used to improve the accuracy of network prediction. Convenient relevant inputs include simple, unambiguous and readily accessible data related to the player's physical characteristics and skill level, such as the player's sex, height, age and playing handicap or other measure of playing skill.

Although apparatus required to compile the training database is the same or similar to that already described, the apparatus used to determine a player's NJPs in this alternative embodiment only requires force plates, communication means, processing means and software means either comprising or having access to the trained neural networks. The processing means and communication means may comprise a portable computer.

Vertical and side GRFs are determined for the player's left and right feet, over the course of the swing, using a side-by-side pair of force plates, similar to those described in the first embodiment. In an alternative lower-cost variation of the second embodiment, the side-by-side force plates are operable only to determine vertical forces and the neural networks training inputs do not include side forces. The former arrangement has the relative advantage of capturing all available information and potentially producing greater accuracy. The latter arrangement has the relative advantages of lower cost, simpler construction and potentially reduced weight and thickness. The player executes the golf swing, standing in a natural position with one foot on each force plate. Signals from the force plate sensors are fed to the processor where they are converted into required input signals for the artificial intelligence system. Where force plates solely determine vertical forces, the signals are converted to eight such inputs, these being the vertical force on the left foot and on the right foot, and the horizontal components of COP for each foot and of the resultant for both feet. Where force plates additionally determine side forces, the signals are converted to additional inputs. Where vertical forces are solely determined, other means for determining vertical GRFs may be considered, including high-speed pressure pad arrangements determining variable force and encompassing both feet. Pressure pads typically have the relative advantages over force plates of lower cost and requiring less structural strength but typically have the relative disadvantage of lower responsiveness and lower accuracy at high speed.

FIG. 14 shows a diagram depicting some of the steps involved in the alternative embodiment for predicting or determining end-use NJPs using a trained artificial intelligence, as described above. The abbreviation NN signifies 'neural network'.

The alternative embodiment using artificial intelligence has various relative advantages compared to the direct measurement or determination embodiment earlier described, including the following. The player makes no contact with the apparatus, other than to stand on the force plate platforms. The apparatus can be operated by the player without external assistance by an expert or third party. It is of much lower unit cost and involves very little user effort in preparation or set-up. It is more compact, lighter, more robust and effectively maintenance-free. It is also more easily transported and stored. Balanced against this, the alternative embodiment has various relative disadvantages compared to the direct measurement or determination embodiment, including the following. It can only determine or predict parameters which have been measured or determined by other apparatus and is therefore dependent on the capabilities of other apparatus, including their level of accuracy and their limitations in measuring or determining parameters. In general, it is likely to be much less accurate. As a product, it has much higher one-off starting costs, requiring the compilation of a large training database and preparation of neural networks. It is less capable of recreating a high accuracy visual representation of the swing. It is less capable of determining other parameters of the swing, including kinematic parameters.

Alternative Embodiment of the Invention which Predicts Kinetic Parameters Using Artificial Intelligence Means and an Optical Depth Determination Camera An alternative embodiment of the invention shall now be described for determining or analysing kinetic and kinematic characteristics of a golf swing, where the determination means includes a GRF determination means and an optical depth determination means, such as a 3D camera which comprises inbuilt software capable of image processing, extraction of a jointed segment model of a human subject and motion tracking of the jointed segment model. As previously mentioned, systems with inbuilt software of this type, may be referred to as 'enhanced 3D cameras' and are widely used in computer based gaming, are compact and relatively inexpensive.

The determined characteristics may include kinetic characteristics such as NJPs. The system is operable to combine and process data obtained from the GRF determination means and optical depth determination means to determine or predict new or improved data related to the swing. The process of combining and processing utilises memorised or otherwise available predetermined data related to the swing. The results are synergistic and provide data which cannot be determined with the same levels of accuracy or with the same levels of reliability by either the GRF determination means acting alone or the optical depth determination means acting alone. The process of combining and processing is carried out by an artificial intelligence means which may, for example, comprise one or more neural network systems, where the predetermined data, related to the motion, comprise the network training inputs.

Figure 15:
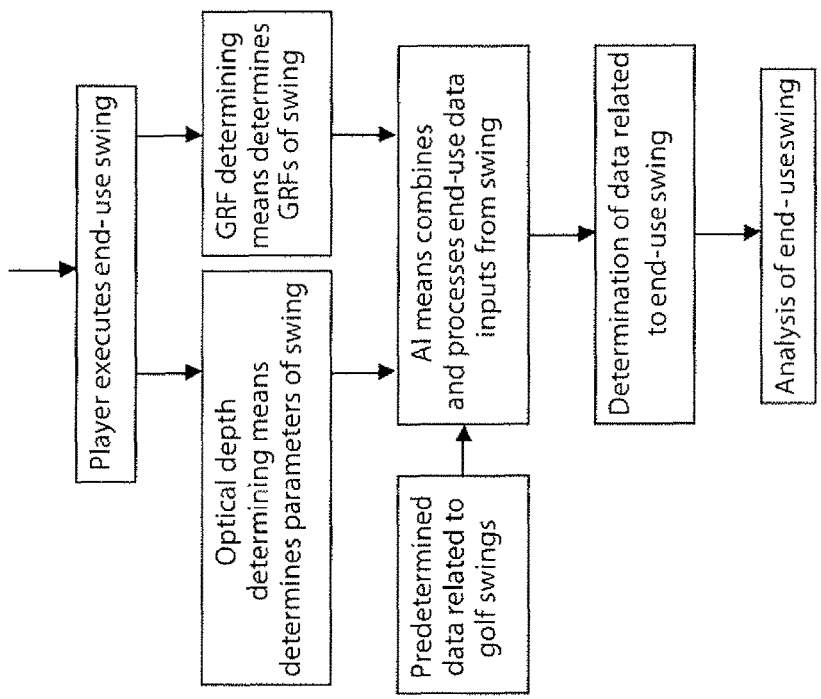

FIG. 15 shows a diagram depicting some of the basic steps involved in the alternative embodiment, as described above, where it is used to determine or predict new data in an end-use swing and to analyse the swing. The abbreviation AI signifies 'artificial intelligence'.

The optical depth determination means may comprise a 3D camera or enhanced 3D camera, of same or similar type to that described earlier for determining a player's BSIPs.

In this instance, the ability to determine depth is of particular use in distinguishing outlines of objects positioned at different depths, such as a club or player's limbs distinguished from a background or player's body, rather than precise measurement or determination of the 3D contours of the surface as used in the instance where BSIPs are determined. Distinguishing such outlines is of particular importance in enabling the enhanced 3D camera to identify and extract a jointed figure from captured images.

An example of the alternative embodiment shall now be described. The apparatus of this embodiment comprises an enhanced 3D camera, a pair of force plates, a processing means and a communication means. The force plates are operable to determine GRF data. The enhanced 3D camera is operable to extract images or motion showing a jointed model with rigid segments from the captured 3D images or motion. Data is combined and processed using an artificial intelligence system of neural networks trained from a large representative database of golf swings.

Figure 16:
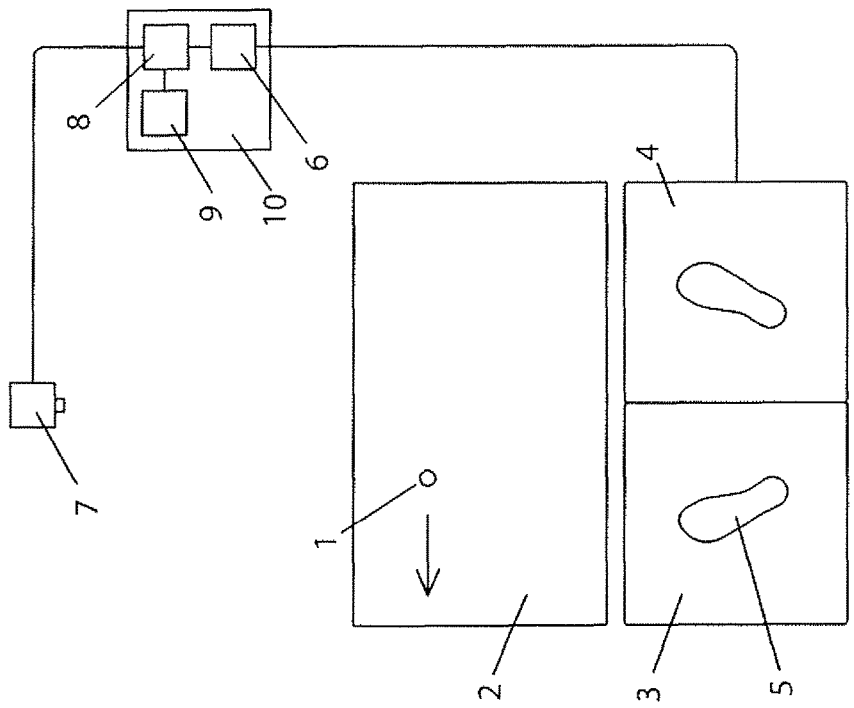

FIG. 16 shows a schematic plan view of an example of such apparatus. An index of reference numerals used in the figure is shown below.

1. Ball in tee or starting position. The ball is hit in the direction of the arrow.
2. Artificial playing surface.
3. Left foot force plate.
4. Right foot force plate.
5. Player, represented by outline of feet.
6. Processing and interface unit for force plates.
7. 3D camera, facing the player.
8. Apparatus processor.
9. User interface and communication means.
10. Enclosure containing electronic devices.

An aspect of the invention relates to an insight that data obtained by GRF analysis and data obtained from enhanced 3D cameras tend to have opposite strengths and weaknesses and thus can be synergistically combined, subject to a suitable combination method being conceived and provided. Enhanced 3D cameras and their associated software are capable of reproducing certain aspects of the golf swing with good levels of accuracy. These include overall 3D visual representations of stationary or relatively slow moving components of the player and club, and representations of the player shown with proportions which have good visual accuracy. Enhanced 3D cameras perform poorly at measuring or determining objects or parameters which are not clearly presented in the view of the camera. This includes certain types of rotational movements and movements that are fully or partly obscured. It also includes parameters which are essentially kinetic in nature. Enhanced 3D cameras also perform poorly at measuring or determining fast moving components due to their relatively slow frame rate, which is typically around 30 frames or images per second. Where club head speed is at a typical value of around 50 m/s approaching impact, the club head would travel more than 1.6 meters between images if it retained its speed at this critical period of the swing. In contrast, GRF analysis is captured at much higher scan rates, with a practical upper limit which exceeds data capture requirements. It is also better at detecting fast moving objects in the sense that these tend to generate higher forces which are more easily detected as GRFs. GRF analysis is unaffected by the visibility of movements and is inherently suited to determine kinetic parameters, because of the kinetic nature of GRFs. GRF analysis performs relatively poorly in reconstructing overall 3D visual representations of objects such as the player.

GRFs are determined in an end-use swing by means such as those already described in other embodiments of the invention. GRF signals are fed to the processor means where they are converted into required input signals for the artificial intelligence system. These end-use inputs shall be generally referred to as 'GRF inputs'.

The enhanced 3D camera may be of same or similar characteristics to that already described in another embodiment of the invention. It is of known mass-produced, low-cost type, operating at a frame rate of not less than 30 frames per second. It is provided with supporting software which is operable to extract a jointed model of the subject from the 3D images. The camera is directed to face the player, orthogonal to the target direction, during the swing. Using various known techniques, the camera images are converted to a 3D jointed segment model of the swing movement. The camera supporting software may be modified or augmented to increase the accuracy of tracking a golf swing. For example, where the software is of the type which chooses the nearest match from a library of poses, additions may be made to this library of poses to include those types of poses which typically occur in golf swings. Data is extracted from the 3D jointed segment movement to derive inputs for the artificial intelligence system which determines, or leads towards determining, the required kinematic and kinetic parameters. These end-use inputs shall generally be referred to as 'camera inputs' where used as inputs to the neural networks. The enhanced 3D camera can also determine useful parameters independently of the GRF determination system. These include parameters related to BSIPs, times related to stationary or low speed motions such as address, takeaway, top-of-backswing and end of follow-through, and visual representation of the player and club.

The artificial intelligence system comprises a set of neural networks trained to predict different required end-use outputs using various sets of end-use inputs. Usually the network end-use inputs will include all significant GRF inputs and selected camera inputs. Other end-use inputs which are not GRF or camera inputs may also be used. Different networks can be advantageously used for different types of swings, including swings with different club types, such as different numbered woods and irons.

The networks are trained with training inputs comprising GRF training inputs and non-kinetic training inputs equivalent to end-use camera inputs, and training outputs comprising high-accuracy measurements or determination, for individual player swings recorded in the database. These training tests are carried out over a large number of swings across a large number of players representing the range of skills, techniques and faults likely to be encountered when the trained network is later put to use. These training tests may, for example, be carried out by apparatus such as that described earlier in this specification using a magnetic motion capture system. Kinematic training inputs equivalent to end-use camera inputs, such as linear and angular speeds and accelerations of segments, can be measured by a magnetic motion capture system. An example of a training input being 'equivalent' to an end-use camera input is given by the angular velocity of the club shaft projected in the frontal plane, which is the vertical plane facing the camera. This input can be determined both by the magnetic motion capture system and the enhanced 3D camera, and expressed in identical equivalent values of, say, degrees per second. Static training inputs equivalent to end-use camera inputs, such as measurements of joint positions and segment lengths, can also be measured by the magnetic motion capture system and stylus.

End-use camera input parameters related to BSIPs may be presented in a manner suitable for inputting to the neural networks. For example, they may be represented by one or more values describing a particular BSIP characteristic known to affect the golf swing across a graduated range. Such graduated ranges may include appropriately modified male and female varied morphological ranges such as endomorphic, mesomorphic and ectomorphic ranges. They may also include ranges of player heights, or player height to weight ratios. End-use camera inputs related to weight may also utilise information on weight obtained from GRF data, which correspond to the player's weight when the player is at rest. Each of these ranges may be represented by simple normalised scales running from zero to unity. End-use camera inputs and training inputs are calculated on the same basis. Data related to camera input BSIPs can be determined in a manner similar to that already described for determining BSIPs using an enhanced 3D camera in the previously described embodiment using magnetic motion capture methods.

The neural networks may also be trained with data from optical depth determination parameters which are of equivalent type to data which can be obtained from end-use optical depth determination parameters. For example, where similar or identical types of enhanced 3D cameras are used when determining training inputs and when determining end-use inputs, and where the enhanced 3D cameras match an image to an image from a library of poses, a training input may comprise a sequence of identifying labels on matched images which occur as a swing progresses through the relevant portion of the training swing. The corresponding end-use input will comprise the sequence of identifying labels on matched images which occur as the end-use swing progresses through the corresponding portion of the end-use swing. Inputs of this type can also be used with 3D cameras which are not enhanced 3D cameras, the apparatus processor fulfilling the functions otherwise carried out by the enhanced 3D camera processor. Various other types of optical depth determination training inputs can be usefully used with both types of cameras, depending on the types and capabilities of the cameras. In some circumstances it may be necessary to position the training and end-use cameras in similar positions relative to the training and end-use players, respectively. However, with certain types of camera inputs, data are converted by the system processors to 3D representations of the jointed figures and in these instances the systems are substantially insensitive to the relative positions of the training and end-use cameras and players.

End-use GRF parameters and optical depth determination parameters may be determined simultaneously or at separate times. Simultaneous determination is advantageous when determinations from both systems are of related types and are synchronised when being combined and processed, for example where GRF parameters and depth determination parameters comprise equivalent inputs. Where GRF parameters and depth determination parameters are not of related types or synchronised, such as information related to stationary positions, it may prove more convenient to carry out these determinations at separate times.

The end-use network outputs comprise kinetic parameters, including NJPs. They also comprise kinematic parameters, such as segment linear and angular speeds and accelerations, and parameters required to drive a mannequin model of the player though the swing, operable to run in slow motion where required.

Figure 17:
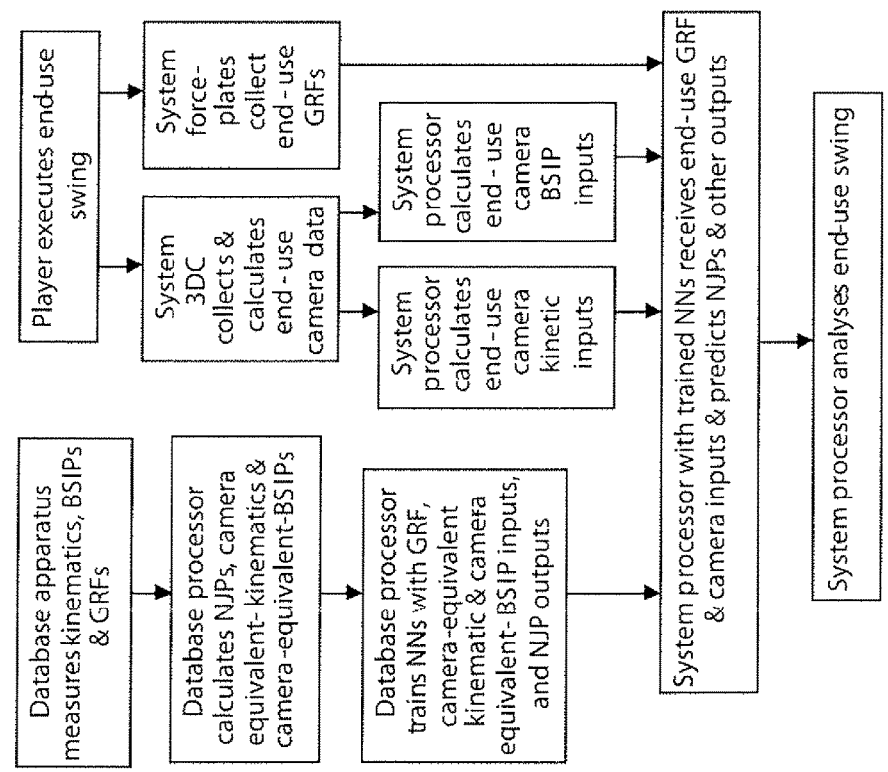

FIG. 17 shows a diagram depicting some of the steps involved in the example of the alternative embodiment for determining or predicting NJPs and other parameters using an end-use GRF determination means, an end-use enhanced 3D camera and an artificial intelligence, as described above. The abbreviations NN and 3DC signify 'neural network' and '3D camera', respectively. The terms 'database apparatus' and 'database processor' refer to apparatus used in compiling the database and training the neural networks. The term 'system' refers to apparatus used in determining and analysing the player's swing. In this example, a 3D camera is not used in the training phase and 3D camera inputs are not held in the database.

Words relating to 'determining' and 'predicting' should be understood to be synonymous in relation to outputs from neural networks or artificial intelligence. The term 'end-use' refers to ultimate use of the invention, for example a neural network is trained with test swings or database swings but is ultimately used to analyse end-use swings.

Alternative Embodiment of the Invention Comprising an Apparatus and Method which Analyses and Interprets Kinetic Parameters The present invention also provides a system and apparatus for analysing a golf swing which includes interpreting and communicating energy generation or transfer parameters of the swing. These parameters may be determined by any of the previously described embodiments of the invention. Further inventive aspects relate to the following realisations and disclosures.

Energy generation in the patterned, high acceleration golf swing, principally occurs in discrete work blocks related to specific joints, where the body is modelled as a system of substantially rigid body segments connected by such joints. For convenience, such blocks of energy related to work done by specific joints shall henceforth be referred to as 'blocks'. Energy associated with joints differs from energy associated with segments, in that at any point in time the most relevant parameter at the joint is joint power or the rate at which energy is being generated at the joint whereas a relevant parameter at a segment at a point in time is its kinetic energy.

Joint power curves, over a period of time, are associated with energy generated by the joint which is represented by the area under the curve. Thus blocks comprise relevant parameters of joint power and blocks of energy associated with the particular time-varying joint power curve. Blocks can be accurately measured for typical analysis or coaching procedures using apparatus and systems operating with convenience and at low-cost, as disclosed elsewhere in this specification. Apparatus or systems with such capabilities are unknown in prior art. Analysis can be advantageously communicated to a human or to a processor means, as a sequence of blocks, set against time or any relevant chronological variable. Where appropriately presented, such analysis can be readily and intuitively understood by non-technical or non-specialist people, including coaches and players.

In accomplished play, positive blocks usually largely comprise a ramp-up, a hold and a ramp-down portion. These are believed to be associated with subconscious communications from the brain and central nervous system instructing the muscle group to ramp-up torque at the joint from a negative, zero or low level, hold the torque at a steady or moderately increasing or decreasing level, and then ramp-down the torque back to a low, zero or negative level.

Measurable relevant positive blocks for a swing typically include those associated with the following joints: right and left ankles; right and left knees; right and left hips; lumbar; thorax; neck; right and left inner shoulders; right and left outer shoulders; right and left elbows; right and left wrists and the grip between hands and club. Since each joint will usually produce at least one block, and some will produce two or more blocks, the overall number available for analysis may vary from about 18 to several times that number. An aspect of the present invention includes an insight that sets of blocks are amenable to intuitive personal analysis if sets of reduced numbers of blocks are simultaneously analysed, and the sets are chosen where useful or meaningful interrelationships are perceived to exist between the blocks of the set. The extent to which block numbers should be restricted in a single simultaneous analysis will depend on the knowledge and experience of the user. For example, an amateur player analysing his own swing will require a simpler analysis with smaller numbers of blocks than a professional coach with long experience of viewing such analyses. A typical number limitation for amateur players is about eight, where this refers to the number of different joints or combinations of joints being analysed. The equivalent typical number limitation for experienced analysts is about twelve. For most studies, analysis is also facilitated by restricting the temporal period to the downswing, since backswing joint power is of relatively small magnitude and follow-through joint power is relatively less important because it follows the all important impact event.

In initial or overview analyses, numbers of blocks are reduced by various means, including the following. Where a joint produces several blocks, those which are small relative to the largest are initially eliminated. Joints which produce relatively small blocks may also be initially eliminated, such as the grip, head and ankle joints. Joints which sometimes operate simultaneously, or are typically perceived by users as a sub-group, may be combined and initially treated as a group. Such groups include right and left wrists; right and left elbows; right and left ankles; right and left outer shoulders; right and left inner shoulders; and the combination of all four outer and inner shoulder joints. Typically, right and left hips, and right and left knees, do not act simultaneously and are less amenable to being grouped in this way.

The number of blocks can also be reduced by selecting sets which facilitate determination of specific initial relationships or comparisons. For example, an important relationship includes proximal-to-distal sequencing of certain blocks, one of which includes target-side hip; lumbar; thorax; combined shoulders; combined elbows and combined wrists. Other such sets include initial analysis of the most powerful joints, namely right hip; left hip; lumbar; thorax; combined right shoulders and combined left shoulders. Further sets of this type include sets comprising lower body and leg joints and sets comprising upper body, arm and grip joints.

The analysis of blocks can also be advantageously facilitated by simplifying the shape of the block by imposing standardised conditions on it. For convenience, blocks which are simplified in this way shall be termed 'simplified blocks'. The purposes of this simplification include elimination of irrelevancies in the plots, smoothing out of irregularities due to noise in the data or amplification of noise in the calculations and to simplification of presentation by emphasising key features of the block and suppressing less important features.

Figure 18:
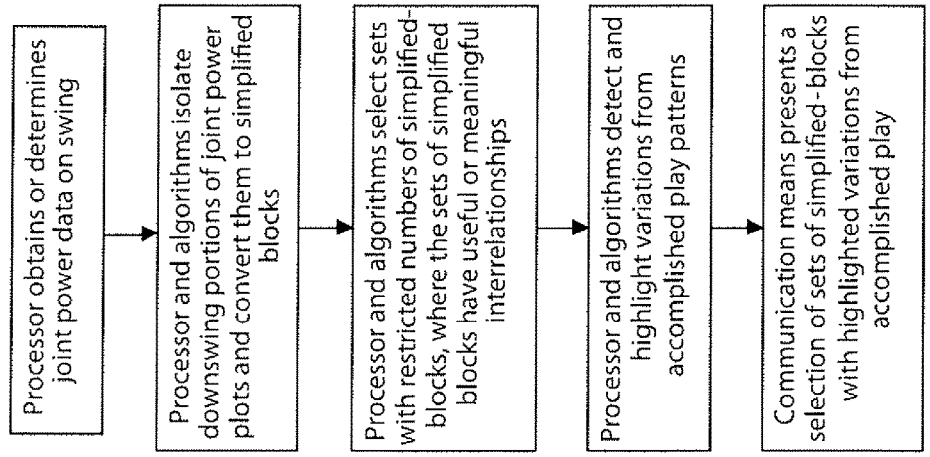

FIG. 18 shows a diagram depicting some of the steps typically involved where an apparatus analyses a golf swing. The apparatus comprises a processor means provided with software and algorithms operable to convert joint power temporal plots to simplified blocks and to select sets with restricted numbers of simplified blocks, where the sets have useful or meaningful interrelationships. In this instance, the processor and algorithms also checks the interrelationships between simplified blocks within sets against what is perceived to represent typically accomplished play. For example, if the basis for selecting the set relates to proximal-to-distal sequencing, then simplified blocks which do not follow the accepted sequence found in accomplished play are highlighted in some way which will be obvious to the user, with the degree of highlighting being varied with the degree to which the simplified block varies from what is perceived to represent typically accomplished play. The communication means presents a menu of the various sets of simplified blocks to the user, who selects sets as required.

Highlighting variations from accomplished play may be carried out in various ways by the apparatus. For example, the outlines of simplified blocks may be coloured to match the joint power which it represents, with typically adjacent simplified blocks being presented in consistent contrasting colours to aid their identification. The centres of the simplified blocks may be coloured or shaded to represent their conformance or variation from what is perceived to represent typically accomplished play. For example, the centres may be coloured in shades of pink to red varying with the degree to which they are judged to match less accomplished play and in shades of light green to mid green varying with the degree to which they are judged to match accomplished play.

Simplified blocks may be constructed from temporal joint power plots in various ways. For example, where the block comprises a plot of positive time-varying joint power and the area enclosed between the plot and the time axis corresponds to the work done, a positive block may be presented as a geometric area above the time axis, bounded by the time axis and the ramp-up, hold and ramp-down plots. Similarly, a negative block may be presented as a similar geometric area below the time axis. In one example of the above, the block is represented by a quadrilateral of four straight lines, with a linear ramp-up, linear hold, and linear ramp-down. In some cases, two of the lines may become collinear such that a triangle results. For convenience, such simplified blocks shall be referred to as 'quads' or as positive quads and negative quads where the joint power is positive and negative, respectively. Joint powers may of course have positive or negative values. Where the value is positive, it signifies an equivalent rate of addition of kinetic or potential energy to the system comprising the player, club, ball and surroundings. Where the value is negative, it signifies an equivalent rate of absorption or extraction of kinetic or potential energy from this system.

Rules, such as those labelled (i) to (iv) below, may be advantageously applied to quads representing energy generation at individual joints. (i) The quad attempts to provide a best-fit for what appears to be a single block of ramp-up, possible-hold and ramp-down of energy generation across a single joint. Outlying straggles of energy generation are ignored. (ii) The quad is such that the area it encloses equals the area enclosed between the actual curve and the time axis, not including any outlying straggles of energy generation. (iii) Lines of the quad attempt a best-fit to the ramp-up, hold and ramp-down portions of the curve. (iv) Where time-varying joint power curve changes from negative to positive, or vice versa, and the areas enclosed between both positive and negative portions of the curve and the time axis are each of sufficient magnitude to warrant separate quads, then the resulting adjacent positive and negative quads should share a common point on the time axis.

With respect to the second rule above, the area between the curve and the time axis may be defined in various ways. For example, it may comprise the entire area from the point where the curve first departs the time axis to the point where the curve finally returns to the time axis. Alternatively, it may comprise the area under the curve from the point where the quad is deemed to start, corresponding to where the ramp-up line meets the time axis, to the point where the quad is deemed to end, that is where the ramp-down line meets the time axis. The latter alternative has an advantage in that the two points on the time axis are clearly defined, whereas in the former example, the curve does not always have a clear starting or finishing point on the time axis, or where such points exist they might not be properly associated with the intended work block and simplified-block.

Figure 19:
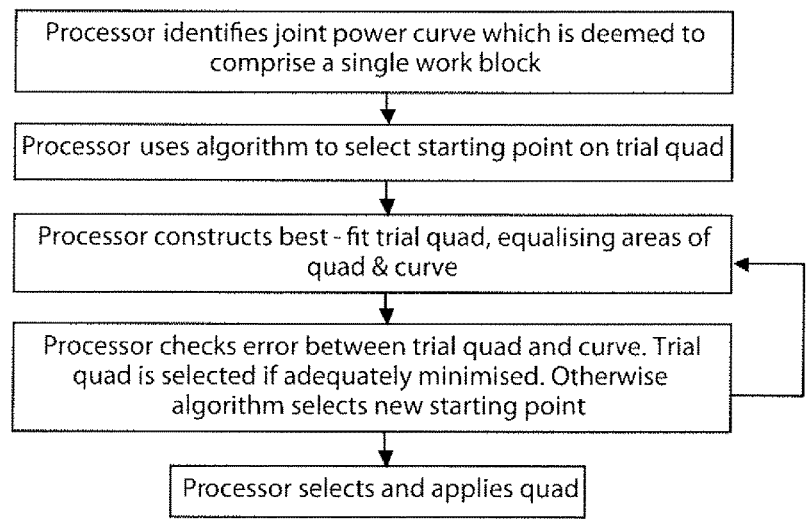

In the present apparatus, where a curve is deemed to comprise a single block, the processor and software automatically determine the quads using the following simple algorithm. A likely trial starting point is selected on the time axis near the beginning of the joint power curve which is to be represented by the quad. Three straight lines, joined end to end, are fitted to the curve with the final point also on the time axis and with the area under the three lines made equal to the area under the curve. These three lines comprise a first trial quad. The sum of the squares of the errors between the trial quad and the curve are computed. A second trial starting point on the time axis, close to the first is then selected and a second trial quad similarly constructed and its error similarly calculated. Depending on the relative magnitudes of the errors, the processor selects additional trial starting points, further back or further along the time axis, homing in to the one which produces the least error, this being finally selected as the presented quad. These basic steps of this process are shown in FIG. 19. The process may be hastened by arranging an algorithm to increase the chances of the first trial starting point falling near the optimum point. For example, a straight line may be best-fitted to a pre-determined proportion of the curve which is likely to be representative of the slope of the ramp-up portion, and the starting point of the trial quad is taken as the intersection of that line with the time axis. The pre-determined proportion may, for example be taken as the first approximate third of the curve to be represented. Alternatively, trialling may commence from the end of curve, in which case the determined proportion may, for example be taken as the final approximate third of the curve to be represented.

Figure 20:
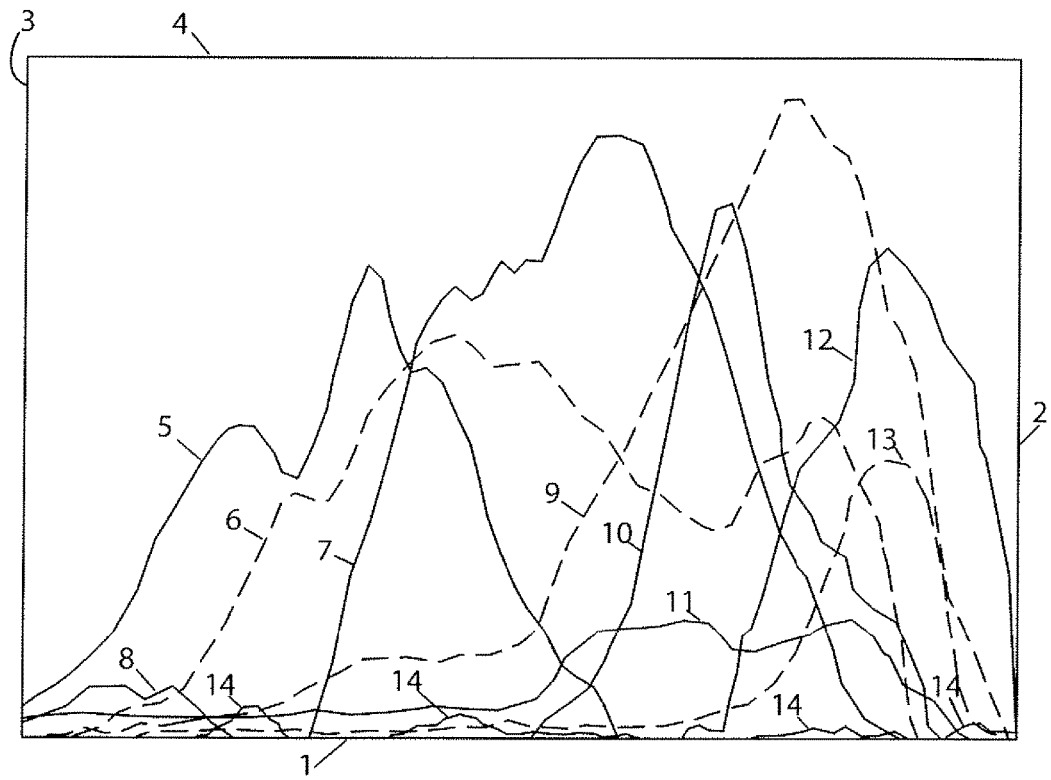
Figure 21:
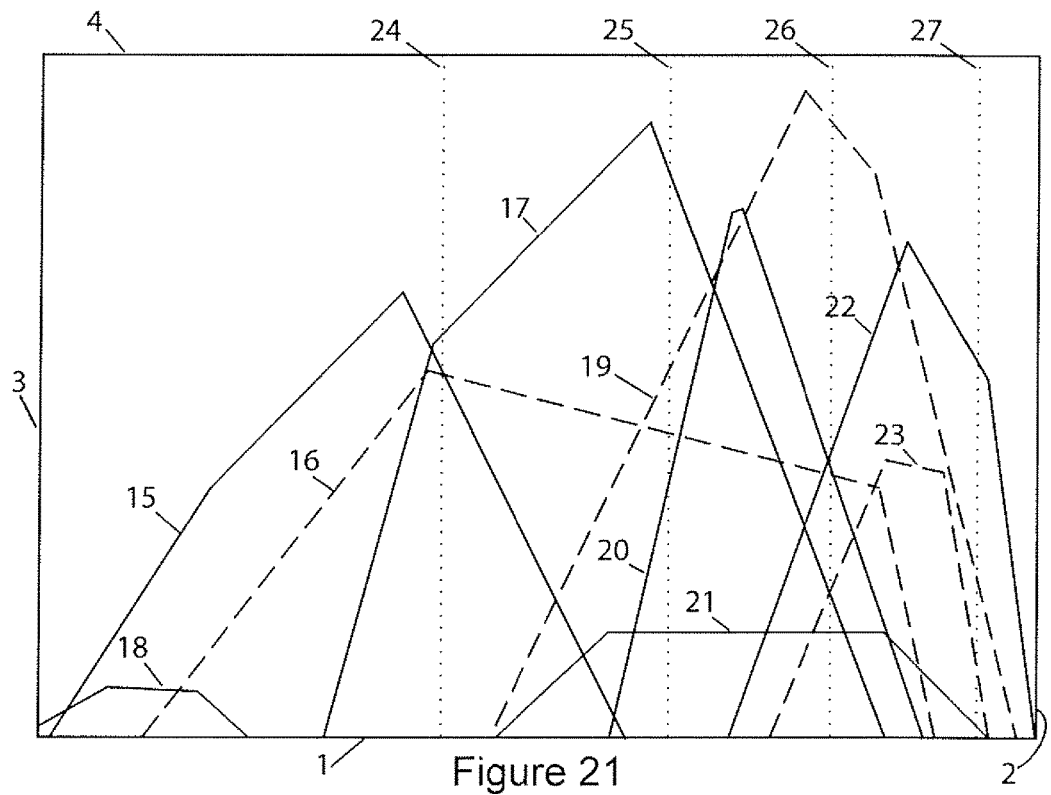
Figure 22:
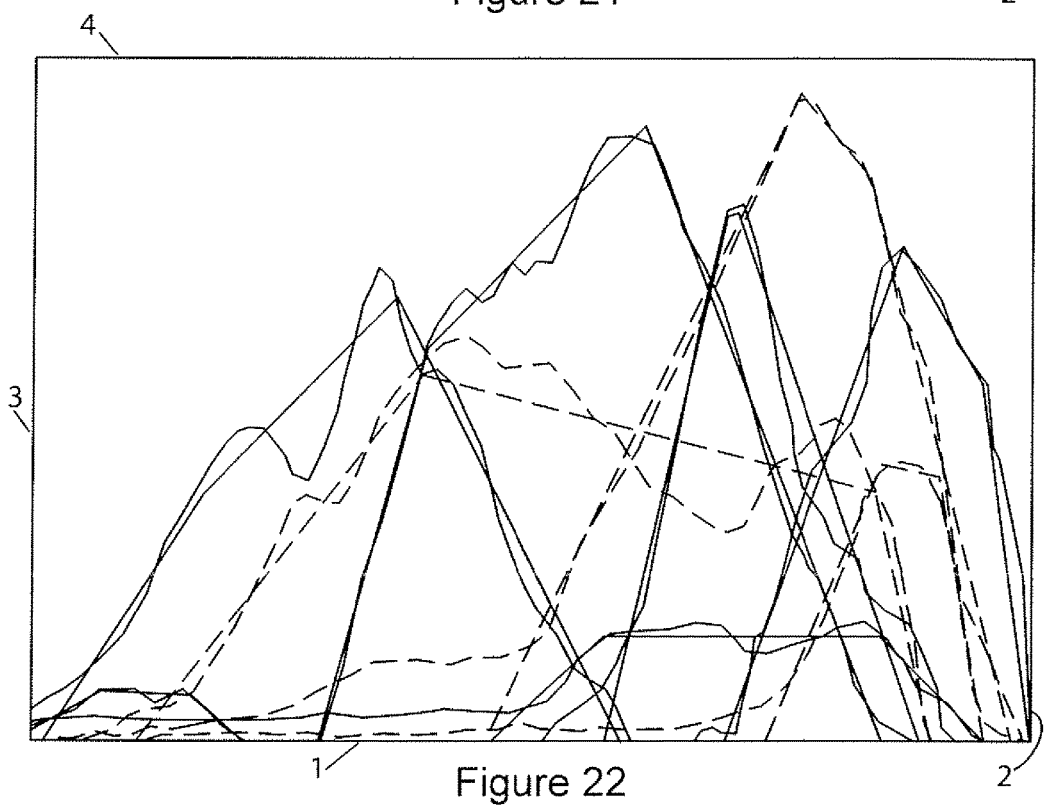

FIGS. 20 to 22 show stages in the construction of a set of quads representing characteristics of a golf swing. An index of reference numerals used in the figures is shown below.
1. Time axis at zero power, from top-of-backswing to impact.
2. Vertical axis and time marker at impact.
3. Vertical axis and time marker at club top-of-backswing, about 0.29 seconds before impact.
4. Upper boundary of plot at joint power of approximately 700 W.
5. Plot of left hip joint power, first major block.
6. Plot of thorax joint power.
7. Plot of lumbar joint power, major block.
8. Plot of lumbar joint power, minor block.
9. Plot of combined shoulders joint power.
10. Plot of right hip joint power.
11. Plot of combined elbows joint power.
12. Plot of left hip joint power, second major block.
13. Plot of combined wrists joint power.
14. Blocks of joint power, associated with joints which also produce blocks of much greater magnitude.
15. Left hip quad, first quad.
16. Thorax quad.
17. Lumbar quad, major quad.
18. Lumbar quad, minor quad.
19. Combined shoulders quad.
20. Right hip quad.
21. Combined elbows quad.
22. Left hip quad, second quad.
23. Combined wrists quad.
24. Vertical time marker where club shaft angle is at 180°, i.e. vertically upwards in the frontal plane.
25. Vertical time marker where club shaft angle is at 135° in the frontal plane.
26. Vertical time marker where club shaft angle is at 90°, i.e. horizontal in the frontal plane.
27. Vertical time marker where club shaft angle is at 45° in the frontal plane.

Referring now to FIG. 20, this depicts a typical set of joint power plots, restricted to the downswing and showing blocks which typically occur with a tendency towards proximal-to-distal sequence characteristics in accomplished play for the left hip, lumbar, thorax, combined shoulders, combined elbows and combined wrists. The left hip is the target-side hip for this and the great majority of right-handed players. Half of the major plots are shown with dashed lines to help distinguish them from neighbouring plots with continuous lines. It will be appreciated that even though the data is restricted to the downswing and limited number of joint powers, it is still relatively difficult to make intuitive sense of the various overlapping plots.

FIG. 21 shows the joint power block plots of FIG. 20 converted to simplified blocks in quad format. Blocks of relatively insignificant size, labelled with reference indices 14 in FIG. 20, have been eliminated. It will be appreciated that the characteristics of the work blocks are simpler and much easier to compare. Their relative sizes, positions, rates of ramp-up hold and ramp-down are relatively clear and obvious. This is particularly the case in an actual displayed set where quads associated with different joints are shown in different contrasting colours, with consistent colours used for particular joints over the range of available plots. The progression of simplified blocks from left to right across a temporal period marked by time and club shaft angle, and representing familiar joints of the body, appears to be capable of being quickly and intuitively understood by almost all players and coaches, even though such simplified blocks actually represent abstract ideas which can never been seen or sensed in reality. It may be readily observed in the diagram that the player's lumbar joint power is unconventional or sub-optimal in two respects. Although lumbar joint power starts before thorax joint power, as would be expected in idealised proximal-to-distal sequence, the initial lumbar joint power is relatively small and terminates before recommencing as a much larger block which commences after the commencement of thorax joint power.

FIG. 22 shows the constructed quads of FIG. 21 superimposed on the joint power plots of FIG. 20.

Various alternative simplified block formats can be used. One of these is similar to the quad format, but uses five straight lines instead of four, again retaining the time axis as one of the bounding lines. The fifth line allows the simplified block outline to better match the shape of the original curve, but complicates construction and reduces the ease with which the presented shape can be understood, since the shape is no longer forced to adopt a single ramp-up, single hold and single ramp-down characteristic.

Another alternative simplified block format comprises bounding the block with a straight ramp-up line, a straight ramp-down line and simple joins or curves, partly following the shape of the original plot, to bridge the gap between ramp-up and ramp-down lines and to join these lines to the base time axis. A simple algorithm is used to match the ramp-up and ramp-down lines to the original plot, and to make the area of the simplified-block equal to the area bounded by the original plot and time axis. The curve portions may follow a best-fit low-order polynomial.

A further alternative simplified block format comprises dispensing with straight lines, other than the time axis, and fitting a smoother curve to the entire original plot, for example by using the curve of a low-order polynomial. Then, as with the previous alternatives, the area of the simplified-block is made equal to the area bounded by the original plot and time axis.

Figure 23:
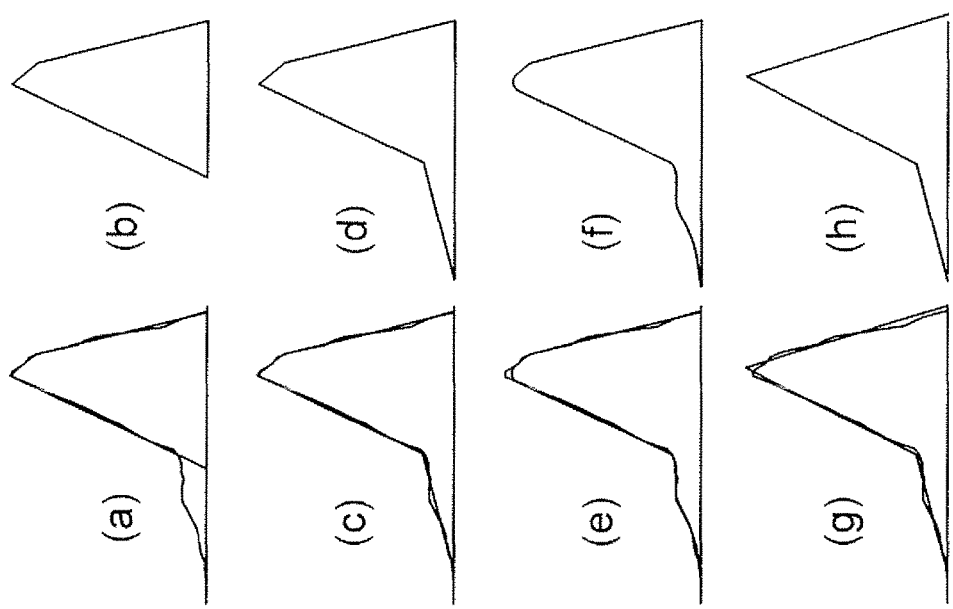

FIG. 23 shows examples of some of these simplified block formats applied to the combined shoulders joint power plot of FIG. 20. View (a) shows a quad fitted to the plot, with the quad shown separately at view (b). It will be appreciated that the quad very accurately depicts the ramp-up and ramp-down characteristics of the plot, but omits the initial low level lead up of joint power present in the joint power plot. View (c) shows a five sided simplified block format fitted to the same combined shoulders plot, with the simplified block shown separately at view (d). In this instance, the entire shape of the plot is very well matched, but the simplified-block has now taken on the complexity of two different ramp-up rates. View (e) shows a format where straight lines are fitted to the ramp-up and ramp-down portions and a low-level polynomial used to bridge the gap between the ramp-up and ramp-down lines and also to fit the gap between the time axis and the ramp-up line. The simplified block is shown separately at view (f). In this instance the goodness of fit of the ramp-down line causes it to continue to the time axis. An example of a low-order polynomial fitted to the entire curve is not shown in the figure because it is very similar to that shown at view (e) and view (f), with the ramp-up and ramp-down lines displaying a slight curvature. Views (g) and (h) show an example of a potential difficulty which can occur if care is not taken to ensure that precedence is given to fitting the ramp-up and ramp-down lines. In this instance, one of the available lines of the quad has been used to represent the initial low level lead up of joint power instead of the hold region between ramp-up and ramp-down. This is normally considered undesirable, and thus the quad algorithm is structured such that major ramp-up or ramp-down events predominate over weaker leading or following portions of joint power.

Different types of simplified block formats can sometimes be advantageously used in analysing a swing. For example, where initial analysis is carried out or where there are a large number of simplified blocks on a display, a simple quad format may provide the best solution. But where more detailed analysis on a specific part of a swing is being carried out, simplified block formats which preserve greater plot detail may provide a more appropriate solution. An algorithm may be used which is operable to automatically switch one simplified block format to another, if the chosen standard format proves inadequate. For example, where a quad format is normally used, but there are two strong ramp-up, or ramp-down, rates present with both having similar levels of significance, the format may automatically switch from a four-straight-line quad to a five-straight-line format for that particular simplified-block.

As previously mentioned, quads and other simplified block formats are geometric representations by a processor of interaction between the player's brain and muscle groups in accomplished play. The quad corresponds to positive individual joint power being subconsciously switched on, held and switched off by the brain in discrete packages and assumes that the control process does not normally appear in any sequence other than being switched on, held and switched off by the brain in discrete packages. Muscle groups associated with most individual joints act in unison such that separate adjacent quads for these individual joints do not overlap but are either fully separate or abut each other as truncated quads or simplified blocks. Sometimes, muscle groups associated with certain assumed joints on the spine, may involve separate muscle sub-groups which do not act in unison. Where this occurs, separate adjacent quads or simplified blocks may overlap.

Blocks of energy corresponding to individual joints may sometimes comprise more than one simplified block or quad. This can occur in at least two different situations. In one of these situations, it appears that an instruction to ramp-down is changed to an instruction to ramp-up by the brain or central nervous system before the block has fallen to zero on the time axis. In this instance, the block is divided into two or more truncated simplified blocks or quads. In another situation, it appears that there is more than one set of muscle groups acting across the same joint and that these separately commence ramp-up and ramp-down of their joint power levels. In this instance, the block is divided into two or more overlapping simplified blocks or quads.

Where a block of single joint power energy is deemed to be a potential candidate for division into truncated simplified blocks or quads, the block is divided if the following criteria are met. The first criterion is that the power curve, representing the block, must comprise at least two maximum peak values and the minimum value between the two peak values must be less than a particular proportion of the lesser of the two peak values. The other criteria relate to proportional values, and may include requirements that the peak value of the resulting divided simplified block or quad exceed a set threshold, its area or energy value must exceeds a set threshold and its area or energy value must exceed a set percentage threshold of the total positive value for the joint. The following criteria have been found satisfactory for low handicap accomplished players. The first criterion is a threshold proportion of about 0.58. The proportional value criteria typically include a threshold peak value of about 7 Watts, an area or energy value of about 0.3 Joules and a percentage of total area or energy value of about 3%. When a block is formed into two truncated simplified blocks or quads, they will comprise a shared vertical side extending from the identified minimum value between the two peaks down to the time axis, but with the simplified block or quads otherwise formed in manner already described. In the case of quads, each of the truncated quads will thus comprise five straight sides, although in some instances, some of these sides may be collinear. The minimum value point will comprise one of the corners of the truncated quad. Blocks split by the above criterion, are further subdivided in the same manner if the same criterion applies to the subdivided part. Where a block has undergone division into truncated quads on both its leading and trailing ends, the resulting double-truncated quad will comprise six sides, and as before, in some instances, some of these sides may be collinear. The minimum value points will comprise two corners of the double-truncated quad.

Figure 24:
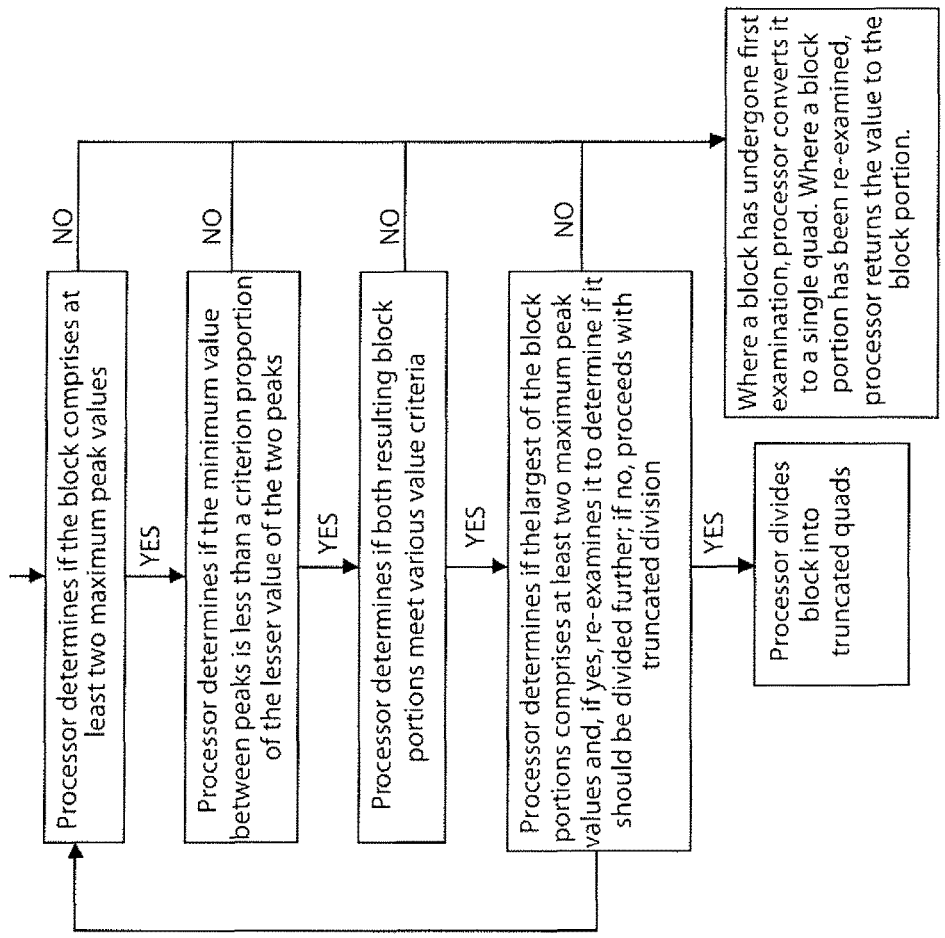

FIG. 24 shows a diagram depicting some of the steps involved in dividing blocks into quads and truncated quads, as described above.

In accomplished downswings, tests have indicated that some degree of overlapping always occurs for quads and simplified blocks of different joints, which is believed to be due to the range of joint motion necessary to power the overall movement. In accomplished downswings, tests have indicated that quads and simplified blocks, related to the same joint, do not normally overlap in the case of the knee, hip, shoulder rotation and elbow joints. However, it appears that they can sometimes overlap in the case of the lumbar and thorax joints. The reason for this is believed to lie with the more complex and disparate nature of the lumbar and thorax joints, where somewhat different sets of muscles are associated with movement in different planes.

FIG. 25 shows various ways that a block comprising a joint power curve can be converted into one or two quads or simplified blocks. An index of reference numerals used in the figure is shown below.
1. Joint power curve.
2. Vertical height of lesser of two peak values.
3. Vertical height of greater of two peak values.
4. Vertical height of minimum value between two peaks.
5. Single quad constructed from joint power curve.
6. First truncated quad constructed from initial portion of joint power curve.
7. Second truncated quad constructed from remaining portion of joint power curve.
8. First overlapping quad constructed from initial portion of joint power curve.
9. Second overlapping quad constructed from remaining portion of joint power curve. This is shown with a dashed outline to distinguish it from the first overlapping quad.

Referring now to FIG. 25, a joint power curve is shown as an example where it is not visually obvious whether it should properly be converted into one or two simplified blocks. An algorithm is used within the processor software to decide on the appropriate conversion strategy using various criteria memorised within the processor system. As previously mentioned, these criteria are set based on empirical analysis of golf swing data to determine whether the block actually represents one or two subconscious instructions from the brain to ramp-up joint power and also whether there is one or two muscle groups acting independently within the block. A criterion based on the proportion of the vertical height of the lesser peak to the vertical height of the minimum value between the peaks, reference numerals (2) and (4) respectively in the figure, may be used as described earlier. Where quad format is used and the criterion indicates that the block should not be split, a single quad will result, typically as depicted by quad (5) in the figure. Where the criterion indicates that the block should be divided into two parts, and just one principal muscle group is involved, then two truncated quads will result, typically as depicted by truncated quads (6) and (7) in the figure. However, where the criterion indicates that the block should be divided into two parts, but two substantially independent muscle groups are involved, then two overlapping quads will result, typically as depicted by overlapping quads (8) and (9) in the figure. The criterion values for division of truncated quads and overlapping quads may differ as they are based on empirical test and observation.

Where the processor presents quads in visual form for a human user, such as on a display screen or a printed document, it has been found advantageous to show familiar time related markers along the time axis. Particularly useful markers include club shaft angle in the frontal plane, at easily understood cardinal positions such as 180°, 90°, 45° and impact which usually occurs close to 0°. These markers may be shown, for example, as vertical lines on the screen or document such as those shown in FIG. 21. Small diagrammatic depictions of golfers in cardinal club shaft positions, corresponding to these vertical lines, can also be useful. Other important landmarks include various points associated with top-of-backswing, such as when hips, shoulders and club reach their maximum rotation positions before commencing their respective downswing movements. The system interface and software may be advantageously arranged to facilitate the user in optionally and individually adding or removing such markers on the display.

Use and Analysis

Analyses of joint power blocks, according to the present invention, can be practically applied to the golf swing using various techniques, including direct analysis of block or quad pattern displays by the player or by an expert, such as a golf coach, or automatic analysis of block or quad patterns by the processor, with the results of this analysis communicated to the player or coach. Where the results are presented in quad or simplified block format, the individual characteristics of each quad or simplified block can be analysed, including its total energy value, its total duration, rate of ramp-up, ramp-down and whether hold value increases, remains steady or falls. The relationship to other quad or simplified block values is also of importance. The relevance of some of these characteristics has already been discussed. Analysis techniques may also involve comparison of the swing quad or simplified block pattern to those of other swings by the same player. The comparison may be made with a player's history of previous swings, for example checking progress as a coaching programme is followed over a period of time. The comparison may also be made with an immediate series of swings, checking the consistency of individual quads or simplified block patterns of the swings. The comparison may additionally be made with swings carried out with other clubs, for example checking how the player translates skills used in long distance clubs, such as the driver, across to swings where maximum distance is not a requirement, but where the same efficient and smooth generation and transmission of energy remains desirable. Analysis techniques may additionally comprise comparison to the quad or simplified block patterns relevant to the equivalent swing or swing range of an appropriate expert model. Criteria may be based on a statistical analysis, for example, of comparisons of individual joint power work magnitudes of quads or simplified blocks represented by their areas, comparisons of the relative coordinate positions of the centroids of quads or simplified blocks, or comparisons of the relative angles of ramp-ups and ramp-downs of quads or simplified blocks. The golf swing is a complex action and further insights can be obtained by comparison to quad or simplified block patterns which are empirically known to produce optimum energy generation and transfer. The expert model is based on a synthesis of swings by expert players, adjusted to be appropriate to the swing and player under analysis. These analysis techniques may be carried out directly by a coach or player or may be automatically carried out by the processor. Previous results from a player may be held in a memory log which may be accessed by the processor and automatically used in the analysis.

Testing and analysis of results using the present invention have indicated the following points. It is a characteristic of more accomplished swings that quads or simplified blocks ramp-up and ramp-down more smoothly and steeply to deliver the required amount of work with a lesser degree of overlapping. They tend to attain correct appropriate proximal-to-distal sequencing. Similarly, tests indicate that in progressively less accomplished downswings, there is a progressively greater degree of overlapping of blocks or quads, less well defined ramp-ups and ramp-downs, and progressively less proximal-to-distal sequencing. It is also observed that significantly more power and energy is typically contained in quads or simplified blocks in progressively more accomplished downswings. Low handicap players are frequently observed to deliver approximately twice as much block or quad power as high handicap players, even though the players may be of similar strength and fitness. Tests additionally indicate that in well and moderately accomplished downswings, players typically repeat very similar quad or simplified block sequences for swings with the same type of club, including quad or simplified block shapes and magnitudes. This feature is of particular significance, because it indicates that players typically have characteristic block or quad signatures which describe their downswings. The feature also facilitates training programmes, where changes in quad or simplified block shapes and sequences can be monitored and used to decide appropriate courses of action. The feature also provides means to check a player's past record of quad or simplified block shapes and sequences where a problem or deterioration has occurred in play Segment Energy Segment energy quads or simplified blocks may also be constructed for blocks of time-varying changes in segment energy represented by the curve of rate of change of segment energy plotted against time across the course of a swing. Unlike joint power quads or simplified blocks, they are associated with segments rather than joints and are more closely associated with energy transfer than energy generation. Although they can be constructed in a similar four-straight-lines format as joint power quads, they differ in that they do not represent ramp-up, hold and ramp-down instructions by the brain or central nervous system, and therefore may also be shown in their original format or in other geometric formats, such as smoothed curves bounded by the time axis. They appear in positive and negative formats, with both types being of importance in the energy transfer process inherent in typical swings. Segment energy blocks may be divided and shown separately for different types of time-varying changes in segment energy, for example separate blocks can be shown for kinetic energy and potential energy.

Segment energy quads or blocks may be advantageously used alongside joint power quads or simplified blocks. They have similar ranges of values as joint power quads or simplified blocks and can therefore be readily shown on the same plots as joint power quads or simplified blocks using the same scales and same units of power on the plot ordinate and units of energy represented by the area under the plot curves. They also tend to occur in characteristic patterns for individual players and these patterns of occurrence have characteristics which correlate with player skills. These features will be familiar to players using joint power quads or simplified blocks and will assist in the development of an intuitive understanding.

The system has the potential to greatly influence coaching methods because of its ability to make complex technical information understandable to a coach or unskilled player, allowing intuitive understanding of subject matter which might previously have been incomprehensible to them. It also allows a large amount of relevant information to be presented on a single chart or screen and overcomes a common aversion to graphically represented information held by many non-technical people.

The invention may be summarised in the following paragraphs:

A system analyses a golf swing, determining individual joint powers generated in a player's body with high levels of accuracy, using inverse dynamics and detailed modelling of the player's body. A depth camera is used to measure body segment shapes and a magnetic motion capture system and 3D force plate system used to measure swing parameters.

The system produces an expeditious analysis without need for highly skilled technical personnel and is suitable for individual coaching and compilation of large golf swing databases.

An alternative system analyses a golf swing, predicting swing parameters, including individual joint powers generated in a player's body, utilising a processor and artificial intelligence means. A depth camera and force plate system are used to measure inputs to the processor and artificial intelligence means. The artificial intelligence means is trained with motion capture, depth camera and force plate related parameters from a large database of golf swings. The system produces an instantaneous analysis and can be used by a player without assistance from a coach or other party.

A further alternative system comprises a processor which analyses a golf swing by converting complex joint power data into a format which extracts and communicates its essential features in a form which can be intuitively understood by a user or more easily processed by further apparatus. The processor utilises special purpose algorithm means to convert joint power data into discrete blocks, selects them into meaningful related groups in restricted numbers, removes insignificant detail and configures their general shapes to highlight basic ramp-up and ramp-down instructions from the player's brain or central nervous system.

It is to be understood that the invention is not limited to the specific details described herein, and that various modifications and alterations are possible without departing from the scope of the invention as defined in the appended method and apparatus claim.

The invention claimed is:

1. An apparatus for providing instructions to adjust a three-dimensional (3D) motion of a golf swing involving a player and club, comprising:
   a motion-capture device for tracking the three-dimensional (3D) motion of the player and the club during the golf swing, the motion-capture device configured to capture the 3D motion as kinematic data that are related to forces that cause or are associated with the 3D motion;
   a processor connected to the motion-capture device and configured to:
   model the player and the club using a plurality of rigid segments and a plurality of joints to represent the player and the club, wherein the plurality of rigid segments are linked using the plurality of joints,
   determine, sequentially joint-by-joint or segment-by-segment in a distal-to-proximal direction or a proximal-to-distal direction along the plurality of rigid segments linked by the plurality of joints, one or more kinetic parameters for each of the plurality of joints that represent the player and the club based on the kinematic data, and
   determine an amount or rate of energy generated across one or more joints of the plurality of joints that link the plurality of rigid segments during the golf swing; and
   an output device that is configured to output instructions based on the one or more kinetic parameters and the amount or rate of energy generated.

2. The apparatus of claim 1, wherein the amount or rate of energy generated includes at least one of energy generated by one or more muscles acting directly about a joint of the plurality of joints or energy generated by a product of torque and angular displacement of adjacent segments about the joint.

3. The apparatus of claim 2, wherein the processor is configured to:
   construct the model of the player in a format relevant to inverse dynamics calculations,
   wherein the motion-capture device comprises a depth determination camera with an inbuilt processor that is configured to extract a jointed segment model of the player.

4. The apparatus of claim 1, wherein the motion-capture device has one or more active sensors positioned on the player or is a photographic motion capture device with one or more passive markers or targets positioned on the player to capture the 3D motion of the player.

5. The apparatus of claim 1, wherein the motion-capture device is a magnetic motion capture device and is configured to directly track a 3D position and 3D orientation of the club and the player in a magnetic reference field, wherein the magnetic motion capture device is configured to:
   directly track the club by tracking a sensor on an upper portion of the club that is below a grip of the club; or
   directly track the player by tracking one or more sensors on the player.

6. The apparatus of claim 1, further comprising:
   a ground-reaction force device for measuring or determining ground-reaction forces during the golf swing and between a ground and a left foot of the player and the ground and a right foot of the player, wherein the ground-reaction force device measures the ground-reaction forces on three mutually orthogonal axes or in a vertical direction, wherein the processor is configured to determine the one or more kinetic parameters further based on the ground-reaction forces.

7. The apparatus of claim 1, further comprising:
   a joint position device configured to obtain a joint position of each joint of the plurality of joints;
   a mass determining device configured to obtain 3D center-of-mass data of each rigid segment of the plurality of rigid segments; and
   a moment-of-inertia device configured to determine 3D moments-of-inertia for each rigid segment of the plurality of rigid segments based on the 3D center-of-mass data and the joint positions.

8. The apparatus of claim 7, wherein the processor is configured to determine the one or more kinetic parameters further based on the 3D moments-of-inertia for each rigid segment of the plurality of rigid segments.

9. The apparatus of claim 7, further comprising:
   a segment shaping device configured to determine a 3D shape or volume of each rigid segment of the plurality of rigid segments, wherein the mass determining device is configured to apply a density to the 3D shape or volume of each rigid segment to obtain the 3D center-of-mass data.

10. The apparatus of claim 9, wherein the segment shaping device includes a palpation device with a stylus sensor, a structured light, a time-of-flight or a stereo imaging depth camera configured to extract a jointed segment model from a set of images.

11. The apparatus of claim 7, further comprising:
    a gravitational force device configured to determine gravitational forces acting on the plurality of rigid segments during the golf swing, wherein the processor is configured to determine the one or more kinetic parameters further based on the gravitational forces.

12. The apparatus of claim 11, wherein the mass determining device is further configured to obtain mass data based on 3D shape or volume data, wherein the gravitational force device is configured to determine the gravitational forces based on the mass data and the 3D center-of-mass data.

13. The apparatus of claim 1, wherein the motion-capture device or processor is configured to measure or determine body segment inertial parameters with respect to 3D geometric shapes including
    calculating shapes and volumes of body segments of the player simplified geometric representations of the plurality of rigid segments of the player.

14. The apparatus of claim 1, wherein the motion-capture device or processor is configured to measure or determine body segment inertial parameters when assisted by palpation by a human operator using the following:
    an implement that is a stylus that is placed at an anatomical landmark,
    wherein the motion-capture device is configured to track the stylus in a reference frame of the motion-capture device; or
    wherein the motion-capture device
    includes a stylus which operates within a magnetic reference frame and is configured to measure, relative to a sensor, positions of points on a surface of the player or the club.

15. The apparatus of claim 7, wherein at least one of the moment-of-inertia device or processor is configured to measure or determine body segment inertial parameters (BSIPs) based on 3D surfaces of the player.

16. The apparatus of claim 15, wherein the moment-of-inertia device or processor is configured to measure or determine BSIPs by moving a stylus tracked by motion capture over representative portions of a segment surface, causing a succession of surface points to be measured and recorded, and continuing to collect points at least until sufficient points have been collected to determine a shape of the segment surface, and then determining the shape of the segment surface from the measured surface points.

17. The apparatus of claim 15, wherein the motion-capture device includes a 3D camera that is configured to determine the 3D surfaces of a body of the player using optical depth determination.

18. The apparatus of claim 15, wherein the motion-capture device includes a 3D camera that is configured to determine the 3D surfaces of a body of the player using optical depth determination and wherein the processor is configured to:
   determine portions of surfaces of segments by optical depth determination when the player executes poses and motions;
   determine 3D shapes of segments from the determined portions of surfaces;
   construct a model of the player with the 3D shapes;
   apply predetermined densities to the 3D shapes; and
   determine BSIPs from the model and densities applied to the 3D shapes.

19. The apparatus of claim 15, wherein the motion-capture device includes a 3D camera that is configured to measure or determine the 3D surfaces of a body of the player using optical depth determination, wherein the processor is configured to:
   determine portions of surfaces of segments of the body by optical depth determination when the player executes poses and motions;
determine 3D shapes of the segments from the determined portions of the surfaces of the segments;
   determine segment reference frames and estimates of joint centers from motion capture of the player executing poses and motions;
   construct a model of the player from the joint centers and the 3D shapes;
   apply predetermined densities to the 3D shapes; and
   determine BSIPs from the constructed model and from the densities applied to the 3D shapes.

20. The apparatus of claim 19, wherein
   optical depth determination and motion capture are carried out simultaneously and
   carried out in a common location.

21. The apparatus of claim 1, wherein the processor is configured to carry out monitoring checks, wherein to carry out the monitoring checks the processor is configured to:
   construct a model of the player and the club using anthropometric landmarks that are measured and recorded, and
   display the constructed model to an operator or user; or
   calculate a length for each of the plurality of rigid segments, and
   check symmetry in the calculated lengths between corresponding pairs of rigid segments that represent a left body part of the player and a right body part of the player.

22. The apparatus of claim 1, wherein the motion-capture device is configured to:
   measure or determine a clubhead speed profile of the club when a clubhead of the club approaches impact with a ball; and
   measure or determine a clubhead speed profile after impact with the ball;

wherein the processor is configured to:
   determine a change in clubhead speed at impact; and
   adjust the clubhead speed profile approaching, through and after impact based on the change in the clubhead speed at impact.

23. The apparatus of claim 22, wherein the processor is configured to:
   detect an impact shock wave at one or more points of the club or the player to determine a time of impact.

24. The apparatus of claim 1, wherein the processor is configured to train an artificial intelligence using ground reaction force parameter inputs and energy parameter outputs;
   use the trained artificial intelligence to predict energy parameters of an end-use swing.

25. The apparatus of claim 1, wherein the motion-capture device includes a magnetic motion-capture device and one or more electronic sensors or emitters, wherein the magnetic motion-capture device is configured to track the one or more electronic sensors or emitters in a magnetic reference field.

26. The apparatus of claim 1, wherein the motion-capture device includes a high-speed camera and one or more passive markers attached to the player, wherein the high-speed camera tracks the one or more passive markers.

27. The apparatus of claim 1, further comprising:
   a joint position device configured to measure a joint position of each joint of the plurality of joints of the player;
   a mass determining device configured to:
      measure 3D shape or volume data of the player; and
      obtain mass data and 3D center-of-mass data of each rigid segment of the plurality of rigid segments of the player based on the 3D shape or volume data of the player;
   a moment-of-inertia device configured to obtain 3D moments-of-inertia for each rigid segment of the plurality of rigid segments of the player based on the 3D center-of-mass data and the joint positions; and
   a gravitational force device configured to determine gravitational forces acting on the plurality of rigid segments of the player during the golf swing based on the mass data and the 3D center-of-mass data;
   wherein the processor is configured to determine the one or more kinetic parameters further based on the gravitational forces and on the 3D moments-of-inertia.

28. A method of providing instructions to adjust a three-dimensional (3D) motion of a golf swing involving a player and club, comprising:
   capturing, using a motion-capture device, the three-dimensional (3D) motion of the player and the club during the golf swing as kinematic data that are related to forces that cause or are associated with the 3D motion;
   modelling, using a processor, the player and the club as a plurality of rigid segments and a plurality of joints to represent the player and the club, wherein the plurality of rigid segments are linked by the plurality of joints;
   determining, using the processor, sequentially joint-by-joint or segment-by-segment in a distal-to-proximal direction or a proximal-to-distal direction along the plurality of rigid segments linked by the plurality of joints, one or more kinetic parameters for each of the plurality of joints that represent the player and the club based on the kinematic data;
   determining, using the processor, an amount or rate of energy generated across one or more joints of the plurality of joints that link the plurality of rigid segments during the golf swing; and outputting, using an output device, instructions based on the one or more kinetic parameters and the amount or rate of energy generated.

29. The method of claim 28, wherein determining the amount or rate of energy generated includes:

measuring energy generated by one or more muscles acting directly about a joint of the plurality of joints; or measuring energy generated from a product of torque and angular displacement of adjacent segments about the joint.

30. The method of claim 28, wherein the motion-capture device has one or more active sensors positioned on the player or is a photographic motion capture device with one or more passive markers or targets positioned on the player to capture the 3D motion of the player.

31. The method of claim 28, wherein capturing the 3D motion of the player and the club includes directly tracking a 3D position and 3D orientation of the club and the plurality of rigid segments, wherein directly tracking the 3D position and 3D orientation of the club and the plurality of rigid segments includes:

directly tracking the club using a sensor positioned on an upper portion of the club that is below a grip of the club; and directly tracking the player using one or more sensors on the player.

32. The method of claim 28, further comprising:

measuring ground reaction forces (GRFs) in three mutually orthogonal axes or in a vertical direction, wherein determining the one or more kinetic parameters is further based on the ground-reaction forces.

33. The method of claim 28, further comprising:

obtaining, using a joint position device, a joint position of the plurality of joints;

obtaining, using a mass determining device, 3D center-of-mass data of a rigid segment of the plurality of rigid segments; and determining, using a moment-of-inertia device, 3D moment-of-inertia data of the rigid segment based on the 3D center-of-mass data and the joint position.

34. The method of claim 33, wherein determining the one or more kinetic parameters is further based on the 3D moment-of-inertia data of the rigid segment.

35. The method of claim 33, further comprising:

determining a 3D shape or volume of each rigid segment of the plurality of rigid segments.

36. The method of claim 35, further comprising:

determining gravitational forces acting on the plurality of rigid segments during the golf swing, wherein determining the one or more kinetic parameters is further based on the gravitational forces.

37. The method of claim 36, further comprising:

obtaining mass data based on 3D shape or volume data; and wherein determining the gravitational forces is based on the mass data and the 3D center-of-mass data.

38. The method of claim 28, further comprising measuring or determining body segment inertial parameters by palpation by a human operator including:

placing an implement that is a stylus at an anatomical landmark; and tracking, using the motion-capture device, the implement in a reference frame.

39. The method of claim 28, further comprising measuring or determining one or more body segment inertial parameters (BSIPs) based on 3D surfaces of the player.

40. The method of claim 39, wherein measuring or determining one or more body segment inertial parameters is based on 3D geometric shapes and includes:

calculating shapes and volumes of body segments using simplified geometric representations of the plurality of rigid segments of the player.

41. The method of claim 39, wherein measuring or determining the one or more BSIPs includes:

moving a stylus tracked by the motion: capture device over representative portions of a segment surface;

measuring and recording a succession of surface points until sufficient points have been collected to determine a shape of the segment surface; and determining the shape of the segment surface from the measured surface points.

42. The method of claim 39, wherein optical depth determination is used to determine the 3D surfaces of the player.

43. The method of claim 39, wherein further comprising determining the 3D surfaces of the player using optical depth determination including:

determining portions of surfaces of segments by optical depth determination when the player executes poses and motions;

determining joint centers and reference frames for the segments;

constructing a model of the player using 3D shapes of the segments fitted to the joint centers and the reference frames;

applying densities to the 3D shapes; and determining BSIPs based on the constructed model and the densities applied to the 3D shapes.

44. The method of claim 43, wherein optical depth determination and motion capture are carried out simultaneously and carried out in a common location.

45. The method of claim 28, further comprising:

constructing a model of the player and the club using anthropometric landmarks; and displaying the constructed model to an operator or user.

46. The method of claim 28, further comprising:

measuring a clubhead speed of the club before impact with a ball;

measuring the clubhead speed after impact with the ball;

determining a change in the clubhead speed at impact; and adjusting a clubhead speed profile before, through and after impact based on the change in the clubhead speed at impact.

47. A method according to claim 46, further comprising detecting an impact shock wave through the club and the player to determine a time of impact.

48. The method of claim 28, further comprising:

training an artificial intelligence using one or more ground reaction force (GRF) parameter inputs and energy parameter outputs; and predicting energy parameters using the trained artificial intelligence.

* * * * *